US011117293B2

(12) United States Patent
Das et al.

(10) Patent No.: US 11,117,293 B2
(45) Date of Patent: Sep. 14, 2021

(54) INTEGRAL INDICATORS FOR SINGLE-PROCEDURE DEVICES

(71) Applicant: Greatbatch Ltd., Clarence, NY (US)

(72) Inventors: Biswa P. Das, Tonawanda, NY (US); Ashish Shah, East Amherst, NY (US)

(73) Assignee: Viant AS&O Holdings LLC, Tempe, AZ (US)

( * ) Notice: Subject to any disclaimer, the term of this patent is extended or adjusted under 35 U.S.C. 154(b) by 602 days.

(21) Appl. No.: 15/886,894

(22) Filed: Feb. 2, 2018

(65) Prior Publication Data

US 2018/0220874 A1    Aug. 9, 2018

Related U.S. Application Data

(60) Provisional application No. 62/454,361, filed on Feb. 3, 2017.

(51) Int. Cl.
| | |
|---|---|
| *B29C 44/12* | (2006.01) |
| *A61B 5/00* | (2006.01) |
| *A61B 90/00* | (2016.01) |
| *B32B 1/02* | (2006.01) |
| *B29C 71/02* | (2006.01) |
| *B29C 44/00* | (2006.01) |
| *A61B 1/00* | (2006.01) |

(52) U.S. Cl.
CPC ......... *B29C 44/12* (2013.01); *A61B 1/00062* (2013.01); *A61B 1/00103* (2013.01); *A61B 5/00* (2013.01); *A61B 90/08* (2016.02); *B29C 44/00* (2013.01); *B29C 71/02* (2013.01); *B32B 1/02* (2013.01); *A61B 2090/0807* (2016.02); *A61B 2090/0814* (2016.02); *A61B 2560/028* (2013.01)

(58) Field of Classification Search
CPC ......... B29C 71/02; B29C 44/00; B29C 44/12; B32B 1/02; A61B 5/00; A61B 2090/0807
See application file for complete search history.

(56) References Cited

U.S. PATENT DOCUMENTS

| 7,811,530 B2 | 10/2010 | Morrison et al. |
| 2006/0111725 A1 | 5/2006 | Biegun |
| 2013/0123821 A1 | 5/2013 | Cobb et al. |
| 2014/0200580 A1 | 7/2014 | Joseph et al. |
| 2016/0022853 A1 | 1/2016 | Hajime et al. |
| 2016/0187309 A1 | 6/2016 | Kang et al. |
| 2017/0007852 A1 | 1/2017 | Isola et al. |

FOREIGN PATENT DOCUMENTS

| WO | 9837819 | 9/1998 |
| WO | 2008104548 | 9/2008 |

OTHER PUBLICATIONS

Extended European Search, Application No. 18155114.4, dated Jun. 20, 2018.
ECA Medical Instruments Disposable Fixation Kit Used in First Surgery to Secure Intelligent Implant Systems Revolution Spine Implant. Business Wire, A Berkshire Hathaway Company, article dated Oct. 7, 2015—WA.
World Health Organization, Patient Safety Health care-associated infections Fact Sheet.

*Primary Examiner* — Walter Aughenbaugh
(74) *Attorney, Agent, or Firm* — Grossman, Tucker, Perrault & Pfleger PLLC

(57) ABSTRACT

Disclosed herein are single-use integral indicators and methods and systems for employing the same. Such indicators and their uses are directed toward identifying and rendering inoperable single-procedure medical devices after their intended—and only—use.

7 Claims, 13 Drawing Sheets

INTEGRAL INDICATORS FOR SINGLE-PROCEDURE DEVICES

CROSS-REFERENCE TO RELATED APPLICATIONS

This application claims priority to U.S. Provisional Patent Application No. 62/454,361 "Low Melting Polymer Part as Single Use Indicator for Single Use Reamers," which was filed on Feb. 3, 2017, the contents of which are hereby incorporated by reference in their entirety.

FIELD OF THE INVENTION

The present disclosure relates generally to single-use indicators for medical devices. In particular, the present technology concerns indicators integral to such medical devices in concert with their application in facilitating a morphological modification to the device following the single-procedure.

BACKGROUND OF THE INVENTION

The following description is provided to assist the understanding of the reader. None of the information provided or references cited is admitted to be prior art.

On a global scale, healthcare-associated infections, i.e., nosocomial infections, impact myriad patients annually, which consequently imparts a considerable mortality rate. To this end, of every one-hundred hospitalized patients at any given time, seven in developed countries, and ten in developing countries, will acquire at least one nosocomial-related disease. See World Health Organization Patient Safety, "Health Care-Associated Infections: Fact Sheet," 2011.

Albeit endemic to all healthcare environments, nosocomial infections are nevertheless markedly higher in low and middle-income countries compared to higher income nations, and more specifically in neonatal patients and those requiring intensive care. See id. And, while urinary tract infections are the most frequent healthcare-associated afflictions in high-income countries, surgical site contamination is the leading cause of nosocomial-based disease in settings with limited resources, affecting up to one-third of surgical patients in those countries. Notwithstanding the demographic character of these hospital acquired infections, nosocomial illnesses beget a substantial economic burden that requires further attention.

Accordingly, there has been a gradual shift in recent years from reusable instruments that potentially harbor infectious pathogens, i.e., to the extent that sterilization procedures break-down or are inadequate, to single-procedure medical instruments which theoretically possess a decreased risk of transmitting a nosocomial disease. The potential for reuse of single-procedure devices, however, cannot be ignored. Whether by mistake, misuse, or reprocessing, circumstances remain in which single-procedure devices are employed beyond their intended lifecycle.

To a large extent, such hazardous recycling of single-procedure devices can be curtailed by implementing a system in which one or more single-use indications conspicuously identify or, more preferably, render inoperative a device after its intended, and presumptive only, use in a medical context. By tangibly impeding second and subsequent uses of a single-procedure device, i.e., pursuant to an irreversible, post-procedure, morphological transformation of the device-making any further exploitation unfeasible-the risk of mistakenly recirculating such a device back into the surgical setting can be significantly reduced. Accordingly, and in view of the foregoing precepts, nosocomial contamination borne out of the improper reuse of single-procedure devices must be addressed. By developing low cost, biocompatible, single-use medical devices designed with integral indicators that capitulate to a single medical procedure, it may be possible to redefine the present nosocomial status quo. See, e.g., Schultz, J. B., "Disposables in the O.R. 'Cover Story: Disposables, ECA Medical Instruments,'" (2013).

SUMMARY OF THE INVENTION

In one aspect, the present disclosure provides an integral indicator for a single-procedure device, which entails a surgical device including (a) at least one integral indicator, where the integral indicator is composed of a polymeric material configured to irreversibly transition from a surgically operative conformation to a surgically inoperative conformation in response to an exposure after the single-procedure, and (b) one or more non-indicator domains that (i) are not composed of the polymeric material, or (ii) remain in the surgically operative conformation in response to the exposure, or the combination of both (i) and (ii).

In illustrative embodiments, the polymeric material possesses chemical and mechanical properties selected from a melting temperature ranging from about 50-121° C., a melt flow rate ranging from about 5-1000 g/10 minute, a tensile strength ranging from about 10-200 MPa, a tensile modulus ranging from about 2-500 GPa, and a strain-at-break ranging from about 2-500%, and combinations thereof. In some embodiments, the polymeric material is selected from polyolefins, polyethylene, polyolefin copolymers, poly(ethylene-co-acetate), polyesters, poly(ethylene-co-acrylate), polycaprolactone and aliphatic homopolymers thereof, polyethers, polyethyleneoxide, fluoropolymers, polypropyleneoxide, olyisoprene, polyamide, polystyrene, polysulphone, polyoxymethylene, polycarbonate, polyvinyl chloride, and acrylnonitrile butadiene styrene, and filled embodiments thereof, and combinations thereof.

The exposure, in certain embodiments, entails subjecting the surgical device, including the integral indicator, to: (i) one or more steam sterilization cycles, or (ii) an average temperature sufficient to precipitate the irreversible transition, or both. In some embodiments, the exposure entails (i) subjecting at least 20% of the total surface area of the integral indicator to one or more steam sterilization cycles, or (ii) subjecting the total volume of the integral indicator to an average temperature sufficient to precipitate the irreversible transition, or both.

In certain embodiments, the surgical device entails a proximal portion and a distal portion, where the integral indicator constitutes at least a section of the proximal or distal portion, or both. In illustrative embodiments, the one or more non-indicator domains are composed of one or more materials selected from metals, metal alloys, shape memory alloys, titanium, nickel, copper, plastics, polymers, ceramic materials, composite materials, and stainless steel, and combinations thereof. In illustrative embodiments, the surgical device is selected from reamers, awls, rod benders, drill guides, guide tubes, distance gages, inserters, implant holders, clamps, portals, screwdrivers, spacers, distracters, plate benders, broaches, fusion plates, fusion screws, spinal rods, spinal connectors, artificial discs, tissue-anchoring devices, fixation devices, dilators, joint spreaders, rasps, fusion cages, shavers, blades, burs, Kerrisons and Rongeurs, and combinations thereof.

In one aspect, the present technology entails a single-procedure indicator system that includes (a) a medical device, and (b) an integral indicator composed of a polymeric material configured to irreversibly transition from an operative conformation to an inoperative conformation in response to an exposure after the single-procedure, (c) where the integral indicator is a contiguous component of the medical device. In illustrative embodiments, the polymeric material possesses chemical and mechanical properties selected from a melting temperature ranging from about 50-121° C., a melt flow rate ranging from about 5-1000 g/10 minute, a tensile strength ranging from about 10-200 MPa, a tensile modulus ranging from about 2-500 GPa, and a strain-at-break ranging from about 2-500%, and combinations thereof.

In illustrative embodiments, the medical device further includes one or more non-indicator domains that (i) are not composed of the polymeric material, or (ii) remain in the operative conformation in response to the exposure, or the combination of both (i) and (ii). In some embodiments, the polymeric material is selected from polyolefins, polyethylene, polyolefin copolymers, poly(ethylene-co-acetate), polyesters, poly(ethylene-co-acrylate), polycaprolactone and aliphatic homopolymers thereof, polyethers, polyethyleneoxide, fluoropolymers, polypropyleneoxide, olyisoprene, polyamide, polystyrene, polysulphone, polyoxymethylene, polycarbonate, polyvinyl chloride, and acrylnonitrile butadiene styrene, and filled embodiments thereof, and combinations thereof. In some embodiments, the exposure includes subjecting the medical device, including the integral indicator, to (i) one or more steam sterilization cycles, or (ii) an average temperature sufficient to precipitate the irreversible transition, or both.

In some embodiments, the one or more non-indicator domains are composed of one or more materials selected from metals, metal alloys, shape memory alloys, titanium, nickel, copper, plastics, polymers, ceramic materials, composite materials, and stainless steel, and combinations thereof. In certain embodiments, the surgical device entails a proximal portion and a distal portion, where the integral indicator constitutes at least a section of the proximal or distal portion, or both. In some embodiments, the medical device is selected from reamers, awls, rod benders, drill guides, guide tubes, distance gages, inserters, implant holders, clamps, portals, screwdrivers, spacers, distracters, plate benders, broaches, fusion plates, fusion screws, spinal rods, spinal connectors, artificial discs, tissue-anchoring devices, fixation devices, dilators, joint spreaders, rasps, fusion cages, shavers, blades, burs, Kerrisons and Rongeurs, and combinations thereof.

In one aspect, the present invention is directed to a method of manufacturing an integral indicator for a single-procedure device, which includes the steps of: (a) selecting a resin possessing a melting temperature ranging from about 38-109° C. and a melt flow rate ranging from about 2-600 g/10 minute, (b) selecting one or more medical device components, and (c) modifying the resin to form a solid polymeric material that is capable of being molded to the one or more medical device components as the integral indicator, where the polymeric material possesses a tensile strength ranging from about 20-400 MPa, a tensile modulus ranging from about 4-1000 GPa, and a strain-at-break ranging from about 4-1000%, and (d) where the integral indicator is configured to irreversibly transition from an operative conformation to an inoperative conformation in response to an exposure after the single-procedure.

In suitable embodiments, the method further entails the step of: (e) determining the chemical and mechanical stability of the integral indicator after being subjected to one or more atmospheric conditioning steps and storage steps, or the equivalents thereof. In illustrative embodiments, the integral indicator is chemically and mechanically stable when it possesses a melting temperature ranging from about 50-121° C., a melt flow rate ranging from about 5-1000 g/10 minute, a tensile strength ranging from about 10-200 MPa, a tensile modulus ranging from about 2-500 GPa, and a strain-at-break ranging from about 2-500%, following the one or more conditioning steps and storage steps, or equivalents thereof.

In illustrative embodiments, the exposure entails subjecting the molded resin as the integral indicator to: (i) one or more steam sterilization cycles, or (ii) an average temperature sufficient to precipitate the irreversible transition, or both. In illustrative embodiments, one or both of the resin and the polymeric material are selected from polyolefins, polyethylene, polyolefin copolymers, poly(ethylene-co-acetate), poly(ethylene-co-acrylate), polyesters, polycaprolactone and aliphatic homopolymers thereof, polyethers, polyethyleneoxide, fluoropolymers, polypropyleneoxide, olyisoprene, polyamide, polystyrene, polysulphone, polyoxymethylene, polycarbonate, polyvinyl chloride, and acrylnonitrile butadiene styrene, and filled embodiments thereof, and combinations thereof. In certain embodiments, the surgical device entails a proximal portion and a distal portion, where the integral indicator constitutes at least a section of the proximal or distal portion, or both.

The methods of the present disclosure include medical device components in some embodiments, where, in such embodiments, the components entail one or more non-indicator domains that: (i) are not composed of the resin or the polymeric material, or (ii) remain in the operative conformation in response to the exposure, or the combination of both (i) and (ii). In illustrative embodiments, the one or more non-indicator domains are composed of one or more materials selected from metals, metal alloys, shape memory alloys, titanium, nickel, copper, plastics, polymers, ceramic materials, composite materials, and stainless steel, and combinations thereof.

In suitable embodiments, the medical device components and the integral indicator are configured as the single-procedure device, where the single-procedure device is selected from reamers, awls, rod benders, drill guides, guide tubes, distance gages, inserters, implant holders, clamps, portals, screwdrivers, spacers, distracters, plate benders, broaches, fusion plates, fusion screws, spinal rods, spinal connectors, artificial discs, tissue-anchoring devices, fixation devices, dilators, joint spreaders, rasps, fusion cages, shavers, blades, burs, Kerrisons and Rongeurs, and combinations thereof.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE FIGURES

FIGS. 4A-4C depict molded Capa™ pellets, while FIGS. 4D-4F show Capa™ barbell molded components, after a 3 minute incubation at 134° C. (FIGS. 4B and 4E) and an 18 minute incubation at 134° C. (FIGS. 4C and 4F), along with Capa™ controls as shown in FIGS. 4A and 4D. FIGS. 4G-4I depict molded grades of Elvax® pellets, and FIGS. 4J-4L show Elvax® barbell molded components after a 3 minute incubation at 134° C. (FIGS. 4H and 4K) and an 18 minute incubation at 134° C. (FIGS. 4I and 4L), in addition to Elvax® controls as shown in FIGS. 4G and 4J.

FIG. 5A is a DSC plot of Capa™ 6500 pellet and barbell molded components, while FIG. 5B shows narrower ordinate-abscissa parameters centered on the melt transition inflection points of the tested polymeric material. FIG. 5C is a DSC plot of Capa™ 6250 pellet and barbell molded components, while FIG. 5D shows narrower ordinate-abscissa parameters centered on the melt transition inflection points in accord with the foregoing.

FIG. 6A is a DSC plot of Elvax® 250 pellet and barbell molded components, while FIG. 6B shows narrower ordinate-abscissa parameters centered on the melt transition inflection points of the tested polymeric material. FIG. 6C is a DSC plot of Elvax® 420 pellet and barbell molded components, while FIG. 6D shows narrower ordinate-abscissa parameters centered on the melt transition inflection points in accord with the foregoing. FIG. 6E is a DSC plot of Elvax® 410 pellet and barbell molded components, and FIG. 6F shows the narrower ordinate-abscissa parameters centered around the melt transition inflection points in accord with the foregoing.

FIG. 7A shows the FTIR spectra for Capa™ 6500 pellet and barbell component parts of the integral indicator, while FIG. 7B shows the spectra for Capa™ 6500 pellets and barbells. FIG. 7C is a narrower ordinate-abscissa parameter spectra highlighting the barbell carbonyl peak for Capa™ 6250, and FIG. 7D concerns narrower ordinate-abscissa parameters centered around the barbell carbonyl peak for Capa™ 6500.

FIG. 8A represents data obtained from Elvax® 250 pellets and barbell molded components, while FIG. 8B shows data pursuant to Elvax® 420 pellets and barbell molded components. FIG. 8C concerns Elvax® 410 pellets and barbell spectra relating to the same.

As shown in FIG. 9A the hardness values of Elvax® 410, Elvax® 420, Elvax® 250, Capa™ 6500 and Capa™ 6250 barbell molds are presented, while FIG. 9B shows hardness values for Elvax® 410, Elvax® 420, Elvax® 250, Capa™ 6500 and Capa™ 6250 barbells pursuant to Shore D evaluations. The tensile strength of Elvax® 410, Elvax® 420, and Elvax® 250 barbells are outlined in FIG. 9C, while FIG. 9D imparts the tensile strength of the Capa™ 6500 and Capa™ 6250 barbells. FIG. 9E reveals the strain at break values for Elvax® 410, Elvax® 420, and Elvax® 250 barbells, while the strain-at-break for Capa™ 6500 and Capa™ 6250 barbell molded components are shown in FIG. 9F.

FIGS. 10A, 10C, and 10E respectively show Elvax® 250, Elvax® 420, and Elvax® 410 barbell molded components prior to the ECAA, while FIGS. 10B, 10D, and 10F respectively show Elvax® 250, Elvax® 420, and Elvax® 410 barbells subsequent to the ECAA evaluations.

FIGS. 11A and 11C respectively show Capa™ 6500 and Capa™ 6250 before the ECAA evaluations, while FIGS. 11B and 11D respectively show the Capa™ 6500 and Capa™ 6250 barbell molded components following the ECAA evaluations.

FIGS. 14B and 14D respectively show an enlarged section of the Capa™ 6500 and Capa™ 6250 DSC plots that highlight the melt transition inflection points.

FIGS. 15A, 15C, and 15E represent Elvax® 250, Elvax® 420, and Elvax® 410 components prior to and after environmental conditioning and accelerated aging (ECAA), respectively. FIGS. 15B, 15D, and 15F show an enlarged section of the resulting data, which highlights the melt transition for the respective data relating to Elvax® 250, Elvax® 420, and Elvax® 410 barbell components prior to and following the ECAA evaluations.

Mechanical property comparisons between the barbell molded components prior to and after environmental conditioning and accelerated aging (ECAA) are shown in FIGS. 16A-16F.

Figure 1:
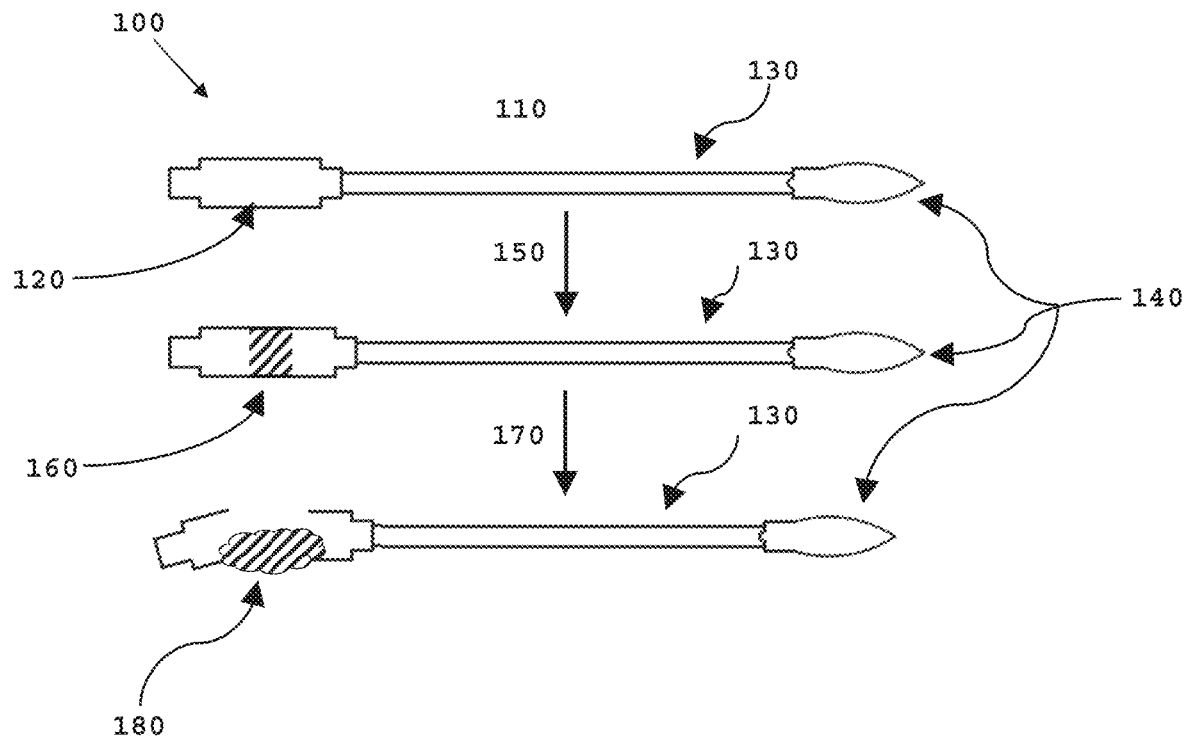
FIG. 1 is a schematic representation of an integral indicator for a single-use medical device prior to and following an exposure.

420, and Elvax® 250 barbells, while FIG. 16F relates to the strain at break with respect to the Capa™ 6500 and Capa™ 6250 barbell components.

DETAILED DESCRIPTION

In the following detailed description, reference is made to the accompanying drawings, which form a part thereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

As used herein, unless otherwise stated, the singular forms "a," "an," and "the" include plural reference. Thus, for example, a reference to "an indicator" can include a plurality of indicators.

As used herein, the term "about" will be understood by persons of ordinary skill in the art and will vary to some extent depending upon the context in which it is used. If there are uses of the term which are not clear to persons of ordinary skill in the art, given the context in which it is used, the term "about" in reference to quantitative values will mean up to plus or minus 10% of the enumerated value.

As used herein, the terms "amphipathic" or "amphiphilic" are meant to refer to any material that is capable of polar and non-polar, or hydrophobic and hydrophilic, interactions. These amphipathic interactions can occur at the same time or in response to an external stimuli at different times. For example, when a specific material or coating, painting, encapsulation, and/or dip coating is said to be "amphipathic," it is meant that such material or coating, painting, encapsulation, and/or dip coating can be hydrophobic or hydrophilic depending upon external variables, such as, e.g., temperature, salinity, pH, etc.

The terms "assessing" and "evaluating" are used interchangeably to refer to any form of measurement, and includes determining if an element is present or not. The terms "determining," "measuring," "assessing," and "assaying" are used interchangeably and include both quantitative and qualitative determinations. Assessing may be relative or absolute. "Assessing the presence of" includes determining the amount of something present, as well as determining whether it is present or absent.

As used herein, the term "biocompatible," refers to, and includes the terms, "biocompatible material," "biocompatible polymer," "biocompatible integral indicator," "biocompatible indicator," "biocompatible materials," "biocompatible polymeric materials," "biocompatible composition," or "biocompatible polymers," which denotes a synthetic or natural material that is, for example, non-toxic to biological systems and/or congruent with biological processes. In this respect, biocompatibility of polymeric materials specify minimal, negligible, or no risk of immunorejection, injury, damage and/or toxicity to living cells, tissues, organs, and/or biological systems. In illustrative embodiments, the biocompatible material is selected from one or more low-melting polymers, polymeric materials, polymers, indicator materials, proximal-end materials, resins, integral indicators, and/or polymers including, for example, but not limited to, polyolefins, polyethylene, polyolefin copolymers, poly(ethylene-co-acetate), poly(ethylene-co-acrylate), polyesters, polycaprolactone and aliphatic homopolymers thereof, polyethers, polyethyleneoxide, fluoropolymers, polypropyleneoxide, olyisoprene, polyamide, polystyrene, polysulphone, polyoxymethylene, polycarbonate, polyvinyl chloride, and acrylnonitrile butadiene styrene, and combinations, monomers, co-polymers, terpolymers and/or salts, esters, and ionized conjugates thereof, and combinations thereof.

As used herein, the term "composition" refers to a product with specified constituents, materials, ingredients, elements, compounds, and the like in the specific amounts or concentrations, as well as any product which results, directly or indirectly, from the combination of the foregoing in the specific amounts or concentrations.

As used herein, the terms "device" or "instrument" refer to a substrate or component, of which an integral indicator is a part of or applied to, where the indictor component is representative of whether the device or instrument has been discharged through use, and is accordingly in an inoperable conformation, i.e., to the extent that it has been subjected to an exposure. Typically, the devices and instruments of the present disclosure relate to single procedure medical devices and instruments, but are not necessarily limited thereto. In suitable embodiments, the medical device has a proximal end and a distal end, and where the integral indicator resides within, or is positioned at or about, the proximal end of the medical device. In suitable embodiments, the proximal end of the device and/or the conflated integral indicator is sufficiently located, configured, arranged and/or positioned on, or with respect to, the medical device such that the indicator region and/or proximal end of the device is not subjected to an exposure until after the single procedure.

In this respect, and in other words, the medical devices and instruments of the present disclosure include a proximal end and a distal end, where typically, for example, the distal end of the device or instrument is the functional region that, in illustrative embodiments, contacts the area of the patient being operated on, e.g., the distal end is typically not the device region contacted by the clinician or surgeon. The proximal end, on the other hand, for example, is the structural region that, in illustrative embodiments, is contacted by the clinician or surgeon. Put simply, the proximal end or region of a medical device typically does not come into contact with a patient's bodily fluids, e.g., blood. In illustrative embodiments, the proximal end of the device is the region that, at least in part, is composed of or harbors the single-use integral indicators disclosed herein.

In some embodiments, the single procedure medical device is a single use orthopedic surgical device, but the medical devise of the present disclosure are not limited thereto. In illustrative embodiments, the medical device or instrument is selected from, but not limited to, single-use reamers, awls, rod benders, drill guides, guide tubes, distance gages, inserters, implant holders, clamps, portals, screwdrivers, spacers, distracters, plate benders, broaches, fusion plates, fusion screws, spinal rods, spinal connectors, artificial discs, tissue-anchoring devices, fixation devices, dilators, joint spreaders, rasps, fusion cages, shavers, blades, burs, Kerrisons and Rongeurs, and combinations thereof.

As used herein, the term "discharge status" of a single-procedure device or instrument refers to the lifecycle status of the device or instrument. In suitable embodiments, for example, a device or instrument that has been "discharged" or "affirmatively discharged," as used herein, is an indication that the status of the device or instrument is an "end-of-use"

status, i.e., the device should not, or physically cannot, be redeployed for a second or repeat procedure.

As used herein, the term "exposure" refers to circumstances where a medical device, instrument, apparatus, biocompatible composition, integral indicator, transitioned indicator, and/or an operable or inoperable integral indicator, alone or collectively, are subjected to one or more conditions, applications, and/or the presence of heat, kinetic energy, elevated temperatures, steam, sterilization, one or more autoclave cycles, high temperature disinfection or washing, the sterile application of steam, or other conditions where the medical device, instrument, apparatus, biocompatible composition, integral indicator, transitioned indicator, and/or an operable or inoperable integral indicator, alone or collectively, are incubated at temperatures sufficient to irreversibly transition the integral indicator from an operative conformation to an inoperative conformation.

As used herein, the term "polymer" refers to a macromolecule made of repeating monomer or multimer units. Polymers of the present disclosure are polymeric forms of, and include, but are not limited to, polyolefins, polyethylene, polyolefin copolymers, poly(ethylene-co-acetate), polyesters, poly(ethylene-co-acrylate), polycaprolactone and aliphatic homopolymers thereof, polyethers, polyethyleneoxide, fluoropolymers, polypropyleneoxide, olyisoprene, polyamide, polystyrene, polysulphone, polyoxymethylene, polycarbonate, polyvinyl chloride, acrylnonitrile butadiene styrene, polyacrylates, polyacrylamides, polyacrylamide copolymers, polyacrylic acid, sodium polyacrylate, potassium polyacrylate, lithium polyacrylate, ammonium polyacrylate, ethylene maleic anhydride copolymer, carboxymethylcellulose, polyvinyl alcohol copolymers, polyethylene oxide, polyacrylonitrile, polylactic acid, polyglycolic acid, poly(lactide-co-glycolide), poly(L-lactide), silicone acrylate, acrylate with enhanced hydrophilic surface functionality, siloxane acrylate, hexafocon A, enflufocon A, enflufocon B, hioxifilcon B, hioxifilcon D, hioxifilcon A, polymacon, methafilcon A, 2-hydroxyethyl methacrylate (2-HEMA), 2,3-dihydrosypropryl methacrylate (Glycerol Methacrylate, GMA), polymethyl methacrylate (PMMA), acrylamide, poly(hyaluronic acid), poly(sodium alginate), poly(ethylene glycol) (PEG), poly(lactic acid) polymers, poly(glycolic acid) polymers, poly(lactide-co-glycolides) (PLGA), poly (urethanes), poly(siloxanes) silicones, poly(ethylene), poly (vinyl pyrrolidone), poly(2-hydroxy ethyl methacrylate), poly(N-vinyl pyrrolidone), poly(methyl methacrylate), poly (vinyl alcohol) (PVA), poly(acrylic acid), poly(vinyl acetate), polyacrylamide, poly(ethylene-co-vinyl acetate), poly(methacrylic acid), polylactic acid (PLA), poly(L-lactide) (PLLA), polyglycolic acids (PGA), polyamides, polyanhydrides, poly(ethylene-co-vinyl alcohol) (EVOH), polycaprolactone, polyvinylhydroxide, poly(ethylene oxide) (PEO), polyorthoesters, poly(N-isopropylacrylamide) (PIPAAm), N,N-dimethylaminopropyl acrylamide (DMAPAAm), poly(N-acryloylpiperidine)-cysteamine (pAP), PIPAAM-carboxymethyl dextran benzylamide sulfonate/sulfate (PIPAAm-CMDBS), N,N-methylene-bis-acrylamide cross-linked polymer, PIPAAm-PEG N-isopropylacrylamide, N,N-dimethylacrylamide, 2-hydroxyethylmethacrylate, N-hydroxyethyl acrylamide, N-vinyl-2-pyrrolidone, 4-pentenoic acid, N-isopropyl methacrylamide, N-methoxymethyl-N-isopropylacrylamide, 2-(dimethylmaleimido)-N-ethylacrylamide, N,N-methylene-bis-acrylamide and PIPAAm-PEG, and monomers, co-polymers, terpolymers thereof, and/or and salts, esters, and ionized conjugates thereof. Non-limiting examples also include one or more of and combinations thereof including cross-linked polymers, co-polymers and/or terpolymers thereof, and filled embodiments thereof, and combinations thereof.

As used herein, the terms "filled polymer," "filled polymeric material," or "filled embodiments," refer to a polymer, polymeric material, biocompatible composition, material, integral indicator, resin, and the like, which has been modified to incorporate extra-polymer materials or components as a composite material. For example, but not limiting in any way, such filled polymeric materials include glass filled polymers, ceramic filled polymers, and carbon fiber filled polymers, polymeric materials, biocompatible compositions, materials, integral indicators, resins, and the like.

As used herein, "prevention" or "preventing" of an infection or condition refers to a method or indicator that, in a statistical sample, reduces the occurrence of the infection or condition in a sample patient population relative to an control sample patient population. As used herein, preventing an infection or condition includes the prevention of heath care associated infections, i.e., nosocomial infections, by preventing a second or subsequent use of a single-procedure medical device or instrument.

As used herein, the terms "resin," "resin material," or "precursor resin," all refer to nonvolatile, solid or semisolid, organic substances, as copal or mastic, that consist of amorphous mixtures of carboxylic acids. Resins may be obtained from certain plants as exudations or prepared by polymerization of simple molecules. Within the context of the present disclosure, moreover, a "resin" or "resins" are typically the precursor material employed to form various components of the devices and medical devices disclosed herein, including, specifically, the integral indicator components of the devices and medical devices of the present invention.

As used herein, the terms "strain-at-break," "strain break," "ultimate elongation," or "elongation to break" refer to the strain on an integral indicator, resin material, or polymeric material when it breaks, which is expressed as a percentage.

As used herein, the terms "substantial" or "substantially" within the context of a "substantially enveloped" surface or region or a "substantially aligned" configuration, refer to, e.g., total or complete envelopment, encapsulation or alignment, and the like, but also includes lesser than complete or total envelopment, encapsulation or alignment, and the like, insofar as the intended purpose for performing the act can be carried out to the same extent as if the, e.g., envelopment, encapsulation or alignment, were total or complete.

As used herein, the term "surgically operative" or "operative," when used within the context of a device or medical device possessing an integral indicator, refers to such devices that, in the absence of any material or critical defects unrelated to the integral indicators of the present invention, are capable of being employed by a clinician for a medical procedure. In contrast, the terms "surgically inoperative" or "inoperative," when used within the context of a device or medical device possessing an integral indicator, refers to such devices that are at least in part composed of an integral indicator, which has, pursuant to an exposure, irreversibly transitioned into a conformation that no longer makes feasible the use thereof in a medical procedure.

As used herein, the terms "tensile modulus," "elastic modulus," or "Young's modulus," refer to the degree of resistance, typically measured in gigapascals (GPa), a material possesses with respect to elastic deformation.

As used herein, the term "tensile strength" refers to the ability of a material to withstand longitudinal stress, expressed as the greatest stress that the material can endure without breaking or fracture. Typically, tensile strength is measured in megapascals (MPa) or pounds per square inch (PSI), where a MPa is equivalent to 145 PSI.

As used herein, the terms "thermoconductive material" or "thermoconductive substrate" refer to a material or structure that is capable of conducting heat, i.e., retaining or changing in response to external heat or energy. Typical thermoconductive materials include, but are not limited to, metals, such as, but not limited to, stainless steel, titanium, nitinol, copper, silver, zinc, magnesium, iron, gold, aluminum, aluminum nitride, aluminum oxide, brass, cobalt, beryllium, and graphite, or any combination thereof.

As used herein, the terms "thermoresponsive material" or "thermoresponsive polymer" refer to, but are not limited to, a composition, material, monomer, polymer, co-polymer, terpolymer, or any combination thereof, that is capable of altering its state or property, i.e., melting, in response to a change in temperature.

As used herein, the term "wettability" or "wetting" refers to the ability of a substance to maintain surface contact with a different substance or surface. Surface contact results from intermolecular interactions between a substance and the contacted surface. Wetting, and the surface forces that control wetting, are also responsible for other related effects, including capillary action or capillary effects. For example, when an indicator adheres to a surface of a device the wettability, or degree of wetting, can be calculated in terms of the force balance between the adhesive and cohesive forces. Wettability can be altered by, for example, adding different combinations and concentrations of materials to, for example, a biocompatible composition.

General Overview

When considering the potential for single-procedure medical devices to become erroneously reintroduced into a surgical setting, i.e., subsequent to its initial—and presumptive only-use, the consequences can be severe. Whether intentional or otherwise, recirculation of single-procedure devices precipitates a non-negligible healthcare expense both from a patient's well-being and an economic standpoint. See, e.g., Schultz, J. B., "Disposables in the O.R. 'Cover Story: Disposables, ECA Medical Instruments,'" (2013). Indeed, the impetus behind the advent of single-use medical instruments emanates directly from a desire to eliminate the transmission of nosocomial pathogens. As single-procedure devices have become commonplace in the healthcare setting, various processes have been implemented to mitigate reprocessing and nosocomial pathogenesis.

Single-procedure instruments, in this regard, provide a measure of mitigation with respect to persistent clinical concerns, e.g., acquired nosocomial infections, and economic costs, e.g., patient treatment and the associated increase in frequency and duration of hospital visits. The advantages of employing single-procedure instruments are not difficult to appreciate. Along these lines, some of the benefits attendant to using single-procedure medical devices include, but are not limited to, (i) decreased thermal necrosis of bone inasmuch as sharp, precise, and accurate, surgical tools do not produce the same frictional consequences and osteological debris associated with the use of dull instruments, (ii) reduced surgical site contamination and accompanying infections, (iii) more efficient hospital inventory management insofar as the inventory burden is lessened with off-the-shelf kits for implants and related procedures, (iv) improved patient safety and clinician confidence, and (v) the elimination of substantial life-cycle support costs and the associated environmental encumbrances, e.g., cleaning, handling and re-sterilization of reusable medical devices.

While there remains a need for readily ascertainable indications that conspicuously identify when single-procedure instruments reach their end-of-use, the global healthcare system will nevertheless remain susceptible to the reintroduction-intentionally or otherwise-of medical devices that have exhausted their intended lifespan until institutional measures are adopted that preclude the possibility of such incautious reprocessing. One approach, in this regard, concerns precepts embodied by the methods, devices, and systems of the present disclosure. To this end, insofar as many single-use instruments are required to undergo some measure of high temperature washing or sterilization following a medical procedure, devices designed to incorporate one or more component indicators that are critical to its structural integrity-as an integral indicator-will be rendered inoperative subsequent to the sterilization, i.e., to the extent that such integral indicators are composed of materials that degrade upon exposure to the elevated temperatures of one or more sterilization procedures or "exposures."

Such integral indicators would markedly decrease, if not entirely abrogate, the possibility of healthcare related infections associated with the reuse of single-procedure devices. Nosocomial infections and surgical errors are coterminous with respect to the use of recycled single-procedure devices, i.e., at least to the extent that post process disinfection and sterilization is typically not extensive, while the cause of field failure concerning single-use devices similarly stems from second or repeated procedures with devices that may only be calibrated for a single procedure. As such, the import of addressing the foregoing issues-by having an integral indication that renders futile the reintroduction of a single-procedure device back into a surgical environment-is manifest, where, ensuring that such devices are not returned to the operating room is a lingering healthcare dilemma.

Following an operation, as noted above, end-of-use single-procedure devices typically undergo one or more disinfection and/or sterilization cycles before they are ultimately discarded. In many instances, such sterilization cycles are performed via an autoclave, where, in the presence of elevated temperatures and pressures, water becomes superheated steam that consequently functions to sterilize the enclosed contents. And, in illustrative embodiments, the single-use integral indicators of the present invention operate in a distinct and irreversible manner, typified by a morphological modification that renders the device inoperable, i.e., pursuant to an exposure to one or more sterilization cycles. This modification, moreover, is a de facto destruction of such a device, where the structural degradation not only imparts visual and tactile indications that the device is at its end-of-use, but also renders it unviable for second or subsequent surgeries. In this respect, the integral indicators of the present disclosure obviate the inventible observational mistakes that accompany non-destructive indicator techniques, e.g., colorimetric indications that healthcare personnel must first ascertain before determining whether the device should be discharged.

Along these lines, previously disclosed indicator techniques, such as, e.g., U.S. Pat. No. 8,567,338, disclosing reprocessing indicators for single patient use medical instruments, and U.S. Pat. No. 8,157,747, describing single-use indicators for surgical instruments, relate to systems employing reversible colorimetric indicators that fail to provide an irreversible and destructive modification to the device following a sterilization process. Equally as important with respect to the disparity between the prior art and the present invention is that the elicited structural deformations-of the single-procedure devices designed to incorporate, and accordingly possess, the presently disclosed integral indicators-are not dependent upon an observer's ability to accurately identify reversible indications that may be less than apparent.

Single-Use Medical Device Integral Indicators and Systems

In accord with the foregoing overview, various aspects of the present disclosure include an integral indicator for a single-procedure device, which entails a surgical device designed to incorporate at least one integral indicator composed of a polymeric material configured to irreversibly transition from a surgically operative conformation to a surgically inoperative conformation in response to an exposure after the single-procedure. The polymeric materials, in this regard, are selected and adapted to confer structural integrity to its complement, single-procedure, device as an integrated indicator component at ambient temperatures, e.g., room temperature.

At elevated temperatures, such as the degree of heat energy consequent to one or more sterilization cycles, however, the polymeric materials of the integral indicators are destabilized and accordingly melt away from the device structure, in illustrative embodiments. In this regard, because the indicators of the present invention are configured as one or more integral components of a single-procedure device, i.e., the indicator is localized to one or more structurally critical regions of the device, following exposure to the elevated temperature of, for example, a sterilization procedure at about 134° C., the resulting device is rendered inoperable inasmuch as the melted polymeric materials can no longer support the integrity of the structurally critical region.

As used herein, reference to a "structurally critical" region of a device denotes any surface area and/or volume pertaining to a device region, where, if impaired as a consequence of heat sterilization, or otherwise, it would be accordingly impracticable for any further medical use. In this respect, the one or more integral indicators of the present invention, which may also be referred to as, e.g., biocompatible thermoplastic polymers, polymeric materials, and/or resin precursor materials, and filled embodiments thereof, typically, but not exclusively, constitute at least a portion of the proximal portion or the distal portion, or both, end of a single-procedure device.

Taken together, the biocompatible thermoplastic polymers, resins, integral indicators, and/or the polymeric materials pertaining thereto, and filled embodiments thereof, of the present invention, must satisfy certain material property requirements to properly function as a structurally stable component, and comport with the profile of a single-procedure device at ambient temperatures, while also maintaining the ability to destabilize the same device in response to an exposure, e.g., elevated temperatures pursuant to one or more sterilization cycles. In this regard, it was determined that ranges relating to the melting point, melt flow rate, tensile strength, tensile modulus, and strain-at-break, as shown in the table below, are requisite material properties that the integral indicator materials must possess in order to function in accord with the present invention. See Table 1.

TABLE 1

Integral Indicator Material Property Requirements

| Melting Pt. | Melt Flow Rate | Mechanical Properties |
| --- | --- | --- |
| From about 50-121° C. following storage and shipping. | From about 5-1000 g/10 minute following storage and shipping. | Tensile Strength of the integral indicator after being subjected to storage and shipping: 10-200 MPa. Tensile Modulus of the integral indicator after being subjected to storage and shipping: 2-500 GPa. Strain-at-Break of the integral indicator after being subjected to storage and shipping: 2-500%. |

In accord with the Table 1 parameters above, Table 2 below recites non-limiting examples of various biocompatible thermoplastic polymers, integral indicators, and/or the polymeric materials pertaining thereto, and filled embodiments thereof, with respect to whether each such material satisfies the material property thresholds for implementation as an integral indicator. See Table 2 (below; where a checkmark "✓" indicates that the material property requirements are satisfied, while materials that do not satisfy these requirements are labelled with an "X" designation). In some embodiments, filled-polymer embodiments of the materials that do not satisfy the material property requirements may then, after incorporation of the filled material, satisfy such requirements.

TABLE 2

| | | REQUIREMENTS | | |
| --- | --- | --- | --- | --- |
| Polymeric Materials | Specific Polymer | Melting Point | Melt-Flow Rate | Mechanical Property |
| Polyolefins | Polypropylene | X | X | ✓ |
| | Polyethylene | ✓ | ✓ | ✓ |
| | Paraffin | ✓ | ✓ | X |
| Polyolefin copolymers | Poly (ethylene-co-acetate) | ✓ | ✓ | ✓ |
| | Poly (ethylene-co-acrylate) | ✓ | ✓ | ✓ |
| Polyesters | Polycaprolactone (aliphatic homopolymer) | ✓ | ✓ | ✓ |
| | Polybutylene succinate (aliphatic copolymer) | ✓ | X | ✓ |
| | Polyethylene terephthalate (semi-aromatic copolymer) | X | X | ✓ |
| Polyethers | Polyoxymethylene | X | X | ✓ |
| | Polyethyleneoxide | ✓ | ✓ | ✓ |
| | Polypropyleneoxide | ✓ | ✓ | ✓ |
| | Polytetrahydrofuron | ✓ | ✓ | X |

In particular, the biocompatible thermoplastic polymers, polymeric materials, and integral indicators disclosed herein, and filled embodiments thereof, possess chemical and mechanical properties that impart the required, temperature-dependent, state to properly function. In some embodiments, one or more of the biocompatible thermoplastic polymers, polymeric materials, and/or integral indicators, and filled embodiments thereof, of the present invention, possess a melting temperature ($T_m$) ranging from about 1-500° C., 5-300° C., 10-200° C., 25-175° C., 35-150° C., or 50-121° C. In suitable embodiments, the melting temperature of one or more of the biocompatible thermoplastic polymers, polymeric materials, and/or integral indicators ranges from about 50-121° C. Likewise, the melt flow rate of one or more of the biocompatible thermoplastic polymers, polymeric materials, and/or integral indicators, and filled embodiments thereof, of the present invention, ranges from about 0.1-9000, 1-7,000, 2-5,000, 3-3,000, 4-2,000 or 5-1000 g/10 minute. In illustrative embodiments, the melt flow rate of the one or more biocompatible thermoplastic polymers, polymeric materials, and/or integral indicators ranges from about 5-1000 g/10 minute.

Continuing with the chemical and physical properties of the aforementioned materials, in this regard, illustrative embodiments of the present invention impart such biocompatible thermoplastic polymers, polymeric materials, and/or integral indicators, and filled embodiments thereof, possessing a tensile strength ranging from about 1-500, 3-400, 5-300, 7-250 or 10-200 MPa. In illustrative embodiments, the tensile strength of the one or more biocompatible thermoplastic polymers, polymeric materials, and/or integral indicators ranges from about 10-200 MPa.

The tensile modulus, moreover, of the one or more biocompatible thermoplastic polymers, polymeric materials, and/or integral indicators, and filled embodiments thereof, of the present invention, ranges from about 0.001-900, 0.01-800, 0.1-700, 1-600 or 2-500 GPa. In illustrative embodiments, the tensile modulus of the one or more biocompatible thermoplastic polymers, polymeric materials, and/or integral indicators, and filled embodiments thereof, ranges from about 2-500 GPa. The strain-at-break of the one or more biocompatible thermoplastic polymers, polymeric materials, and/or integral indicators, and filled embodiments thereof, of the present invention, ranges from about 0.001-900%, 0.01-800%, 0.1-700%, 1-600% or 2-500%. In illustrative embodiments, the strain-at-break of the one or more biocompatible thermoplastic polymers, polymeric materials, and/or integral indicators, and filled embodiments thereof, ranges from about 2-500%.

Further in view of the foregoing material property requirements, and ranges pertaining thereto, the one or more biocompatible thermoplastic polymers, polymeric materials, integral indicators, and/or resins of the present invention include, in some embodiments, but are not limited to, polyolefins, polyethylene, polyolefin copolymers, poly(ethylene-co-acetate), polyesters, poly(ethylene-co-acrylate), polycaprolactone and aliphatic homopolymers thereof, polyethers, polyethyleneoxide, fluoropolymers, polypropyleneoxide, olyisoprene, polyamide, polystyrene, polysulphone, polyoxymethylene, polycarbonate, polyvinyl chloride, and acrylnonitrile butadiene styrene, and filled embodiments thereof, and combinations thereof.

Such filled embodiments entail, in some embodiments, a polymer, polymeric material, biocompatible composition, material, integral indicator, resin, and the like, which has been modified to incorporate extra-polymer materials or components as a composite material. For example, but not limiting in any way, such filled polymeric materials include glass filled polymers, ceramic filled polymers, and carbon fiber filled polymers, polymeric materials, biocompatible compositions, materials, integral indicators, resins, and the like.

The one or more polymeric materials, biocompatible polymers, indicator materials, integral indicators, proximal-end materials, resins, thermoplastic polymers, and/or polymers of the present disclosure may also include, for example, but are not limited to, one or more of polyacrylates, poly-acrylamides, polyacrylamide copolymers, polyacrylic acid, sodium polyacrylate, potassium polyacrylate, lithium polyacrylate, ammonium polyacrylate, ethylene maleic anhydride copolymer, carboxymethylcellulose, polyvinyl alcohol copolymers, polyethylene oxide, polyacrylonitrile, polylactic acid, polyglycolic acid, poly(lactide-co-glycolide), poly(L-lactide), silicone acrylate, acrylate with enhanced hydrophilic surface functionality, siloxane acrylate, hexafocon A, enflufocon A, enflufocon B, hioxifilcon B, hioxifilcon D, hioxifilcon A, polymacon, methafilcon A, 2-hydroxyethyl methacrylate (2-HEMA), 2,3-dihydrosypropryl methacrylate (Glycerol Methacrylate, GMA), polymethyl methacrylate (PMMA), acrylamide, poly(hyaluronic acid), poly(sodium alginate), poly(ethylene glycol) (PEG), poly(lactic acid) polymers, poly(glycolic acid) polymers, poly(lactide-co-glycolides) (PLGA), poly(urethanes), poly(siloxanes) silicones, poly(ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(methacrylic acid), polylactic acid (PLA), poly(L-lactide) (PLLA), polyglycolic acids (PGA), polyamides, polyanhydrides, poly(ethylene-co-vinyl alcohol) (EVOH), polycaprolactone, polyvinylhydroxide, poly(ethylene oxide) (PEO), polyorthoesters, poly(N-isopropylacrylamide) (PIPAAm), N,N-dimethylaminopropyl acrylamide (DMAPAAm), poly(N-acryloylpiperidine)-cysteamine (pAP), PIPAAM-carboxymethyl dextran benzylamide sulfonate/sulfate (PIPAAm-CMDBS), N,N-methylene-bis-acrylamide cross-linked polymer, PIPAAm-PEG N-isopropylacrylamide, N,N-dimethylacrylamide, 2-hydroxyethylmethacrylate, N-hydroxyethyl acrylamide, N-vinyl-2-pyrrolidone, 4-pentenoic acid, N-isopropyl methacrylamide, N-methoxymethyl-N-isopropylacrylamide, 2-(dimethylmaleimido)-N-ethylacrylamide, N,N-methylene-bis-acrylamide and PIPAAm-PEG, including cross-linked polymers, monomers, copolymers, and/or terpolymers thereof, and salts, esters, ionized conjugates, and filled embodiments thereof, and combinations thereof.

The single-procedure devices of the present invention are also composed of one or more non-indicator domains that: (i) are not composed of the polymeric material, or (ii) remain in the surgically operative conformation in response to the exposure, or the combination of both (i) and (ii). In illustrative embodiments, the one or more non-indicator domains are composed of one or more materials selected from metals, metal alloys, shape memory alloys, titanium, nickel, copper, plastics, polymers, ceramic materials, composite materials, and stainless steel, and combinations thereof. Such non-indicator domains, when present, function to facilitate the various material preconditions that may pertain to certain medical devices, including single-procedure devices of the present invention, which are designed to incorporate an integral indicator as detailed herein. In suitable embodiments, non-limiting examples of the one or more non-indicator domains include the distal end or region of the device, the surgically functional domain of the device, one or more shaft or conduit regions, and/or certain portions of the proximal end or region of the device, but only insofar as an integral indicator is not already locally occupying, or intended to occupy, such an end, region or domain.

In this regard, the devices of the present invention typically have a proximal end and a distal end, where, for example, the distal end of the device or instrument is the functional region that, in illustrative embodiments, contacts the area of the patient being operated on, e.g., the distal end is typically not the device region contacted by the clinician or surgeon. The proximal end, on the other hand, for example, is the structural region that, in illustrative embodiments, is contacted by the clinician or surgeon, which typically does not come into contact with a patient's bodily fluids, e.g., blood. In illustrative embodiments, the proximal end of the device is the region that, at least in part, is composed of or harbors the integral indicators disclosed herein. Some embodiments of the present invention, however, provide for various, additional and/or alternative locations on the medical device that encompasses the integral indicator.

The single-procedure surgical or medical device, in suitable embodiments, is selected from one or more reamers, awls, rod benders, drill guides, guide tubes, distance gages, inserters, implant holders, clamps, portals, screwdrivers, spacers, distracters, plate benders, broaches, fusion plates, fusion screws, spinal rods, spinal connectors, artificial discs, tissue-anchoring devices, fixation devices, dilators, joint spreaders, rasps, fusion cages, shavers, blades, burs, Kerrisons and Rongeurs, and combinations thereof. As noted above, such single-use devices and instruments are designed to incorporate the indicators of the present invention as an integral feature, which accordingly imparts a unitary structure that is stable for medical use at room temperature, yet heat labile pursuant to an exposure.

The exposure, along these lines, entails subjecting the surgical device, including the integral indicator, to: (i) one or more steam sterilization cycles, or (ii) an average temperature sufficient to precipitate the irreversible transition, or both, in certain embodiments. More specifically, when the heat of an exposure is applied to the one or more of the polymers, polymeric materials, resins, polymer matrices, and/or indicator materials integral to the single-procedure devices of the present invention, the device is destabilized and rendered inoperable. Such an exposure typically subjects the device-indicator structure to temperatures at or above the melting temperature of the integral indicator. See Tables 1 and 2 above.

In suitable embodiments, the heat energy of an exposure is presented as an elevated temperature, e.g., via steam sterilization, or super-heated steam. In certain embodiments, the heat energy of the exposure occurs via one or more autoclave cycles. Such autoclave exposures can be performed using one or more of a gravity cycle, pre-vacuum cycle, steam flush pressure pulse cycle, and post-vacuum cycles. It will be readily apparent to one skilled in the art that the foregoing and various other high temperature sterilization cycles, as well as other high temperature procedures, can be implemented with respect to the present invention insofar as such cycles entail the requisite temperature, and/or pressures, to transition the integral indicators, in some embodiments, from an operable conformation to an inoperable conformation. In particular embodiments of the present invention, the indicator-incorporated device possess a structural profile that facilitates the melting and consequent dissemination of the melted integral indicator following an exposure, i.e., upon melting, the indicator is able to flow away from the device at least to the extent that re-solidification, post-exposure, is precluded.

In illustrative embodiments, the exposure is one or more autoclave gravity cycles. A non-limiting example of an autoclave gravity cycle concerns a steam sterilization procedure, which entail temperatures ranging from about 100, 150, 200, 300 or 400° C. to from about 125, 250, 400 or 500° C. In some embodiments, the autoclave cycle is performed at about 134° C. The duration of an autoclave cycle, in suitable embodiments, ranges from about 1, 3, 5, 10, 15, 20, 25 or 30 minutes (min) or hours (h) to about from 3, 5, 10, 15, 20, 25, 30, 40 or 50 minutes (min) or hours (h). In some embodiments, the duration of an autoclave cycle is about 18-20 minutes followed by an equal amount of time in a drying cycle.

It will be readily apparent to the skilled artisan that numerous additional variables can impact the rate and extent of integral indicator stabilization, destabilization, transition, modification, polymerization, degradation, decompositions, melting, and/or entropy, etc. Such factors include, for example, percent humidity or hydration, $CO_2$ concentration, pressure, elevation, duration and/or continuity of the supplied temperature, etc., that is associated with an autoclave cycle. The skilled artisan will readily appreciate that appropriate adjustments to the foregoing parameters can optimize the stability and/or destabilization of the integral indicators disclosed herein, i.e., for specific or desired uses.

Concerning the nexus between the elevated temperatures of an exposure, and the melting temperature of the one or more biocompatible thermoplastic polymers, polymeric materials, resins, and/or integral indicators, and filled embodiments thereof, of the present invention, it is important in certain embodiments to consider the extent of device—and specifically, the integral indicator-surface area and volume that will be subjected to such heat energy. Simply put, the integral indicator must be availed to a minimum threshold of localized temperature, for an amount of time, sufficient to achieve the irreversible transition. As such, in illustrative embodiments, the exposure entails: (i) subjecting at least 20% of the total surface area of the integral indicator to one or more steam sterilization cycles, or (ii) subjecting the total volume of the integral indicator to an average temperature sufficient to precipitate the irreversible transition, or both. In some embodiments, the temperature range and duration of an exposure is modified based on the presence of one or more single-procedure device variations, such as, but not limited to, the presence of an insulator material.

Integral indicator embodiment variations, in this regard, include insulated portions or regions of the device, including the integrated indicator, which consequently impacts the temperature range and duration of an exposure required to precipitate the irreversible transition from the surgically operable conformation to the surgically inoperable conformation, in some embodiments. In this respect, the integrally incorporated indicator device typically possesses a structural conformation that is heat-accessible pursuant to an exposure, i.e., such that the energy, in the form of heat, is directly transferred or contacts the polymeric materials of the integral indicator without the addition of a conductor element. This energy transfer, e.g., in the form of heated water or steam, occurs via direct transference or contact with the surface area of the integral indicator, in some embodiments. The elevated temperatures of an exposure, in other embodiments, e.g., such as when an insulator is present, may access or transfer to the polymeric materials of the integral indicator through conduction via a metal conduit.

In some embodiments, both surface area contact and conducted heat transfer occur to precipitate the irreversible transition of the integral indicator from the operable conformation to the inoperable conformation. With respect to the conductance of heat through a suitable metal conduit, such a mechanism is typically not required to the extent that the integral indicators of the present invention are not enveloped by insulator materials. Insofar as such insulator materials are present, and accordingly provide at least a measure of protection from the exposure, heat conductance transfer may be require to morphologically impart the irreversible transition to the inoperable conformation, as detailed herein.

Processes, Applications and Methods of Manufacture

In one aspect, the present invention relates to a method of manufacturing an integral indicator for a single-procedure device, which includes the steps of: (a) selecting a resin possessing a melting temperature ranging from about 38-109° C. and a melt flow rate ranging from about 2-600 g/10 minute, (b) selecting one or more medical device components, and (c) modifying the resin to form a solid polymeric material that is capable of being molded to the profile of one or more medical device components as the integral indicator, where the polymeric material possesses a tensile strength ranging from about 20-400 MPa, a tensile modulus ranging from about 4-1000 GPa, and a strain-at-break ranging from about 4-1000%, and (d) where the integral indicator is configured to irreversibly transition from an operative conformation to an inoperative conformation in response to an exposure after the single-procedure.

In suitable embodiments, the method further entails the step of: (e) determining the chemical and mechanical stability of the integral indicator after being subjected to one or more atmospheric conditioning steps and/or storage steps, or the equivalents thereof, e.g., Environmental Conditioning and Accelerated Aging (ECAA) as further detailed in the Examples section below. In illustrative embodiments, the integral indicator is chemically and mechanically stable when it possesses a melting temperature ranging from about 50-121° C., a melt flow rate ranging from about 5-1000 g/10 minute, a tensile strength ranging from about 10-200 MPa, a tensile modulus ranging from about 2-500 GPa, and a strain-at-break ranging from about 2-500%, following the one or more conditioning steps and storage steps, or equivalents thereof.

As discussed above with respect to Table 1, the biocompatible thermoplastic polymers, integral indicators, and/or the polymeric materials pertaining thereto, and filled embodiments thereof, of the present invention must satisfy certain material property requirements to function as a structurally stable component, i.e., as an integral indicator, of a single-procedure device at ambient temperatures, while also possessing the ability to destabilize the same device in response to an exposure, e.g., elevated temperatures pursuant to one or more sterilization cycles. In this regard, ranges relating to the melting point, melt flow rate, tensile strength, tensile modulus, and strain-at-break, as shown above in Table 1, are requisite material properties that the molded, solid, integral indicator materials of the present invention must possess in order to structurally support the attendant single-procedure device, as well as function in accord with the present invention. See Table 1 above.

However, when manufacturing a single-procedure device that incorporates one or more integral indicators of the present invention, additional design parameters must be taken into consideration with respect to the resin precursor material or materials that are subsequently formed or molded into the polymeric materials of the integral indicator. Such molding, for example, can be conducted using a twin screw injection molding machine. Likewise, environmental conditioning and accelerated aging (ECAA) evaluations reveal even further design considerations that must be accounted for, i.e., when the final single-procedure device design, which incorporates an integral indicator of the present invention, is a commercial product subject to compliance metrics and regulatory oversight.

In this regard, it was determined that ranges relating to the resin melting point, melt flow rate, tensile strength, tensile modulus, and strain-at-break, as shown below in Table 1A, are distinct from the requisite material properties of the final polymeric material constituting the integral indicator after accounting for typical environmental factors, shipping and storage, i.e., pursuant to the ECAA evaluations. See Table 1A below.

TABLE 1A

ECAA Considerations
Integral Indicator & Resin Material Property
Requirements

| Melting Point | Melt Flow Rate (ASTM 1238) | Mechanical Properties |
|---|---|---|
| From about 50-121° C. following storage and shipping. ↕ This can be achieved by using a resin melting point of 38-109° C. | From about 5-1000 g/10 min. following storage and shipping. ↕ This can be achieved by using a resin having a melt flow rate of 2.86-571 g/10 min. | Tensile Strength of the integral indicator after being subjected to storage and shipping: 10-200 MPa. ↕ This can be achieved by employing a molded. indicator Tensile Strength of 20-400 MPa. Tensile Modulus of the integral indicator after being subjected to storage and shipping: 2-500 GPa. ↕ This can be achieved by employing a molded indicator Tensile Modulus of 4-1000 GPa. Strain-at-Break of the integral indicator after being subjected to storage and shipping: 2-500%. ↕ This can be achieved by employing a molded indicator having a Strain at Break of 4-1000%. |

Briefly, it was initially determined that the melting point of the molded resin, i.e., the integral indicator composed of the polymeric material, following storage and shipping, as approximated pursuant to the ECAA evaluations disclosed herein, should range from about 50-121° C. As such, the melting point of the resin must account for any $T_m$ variations that occur pursuant to this molding process, in addition to aging and exposure to variable environmental conditions. In this regard, and as further detailed in the Examples section below, the melting point of the molded resin was determined to be greater than the pre-molded resin.

A similar increase was identified after being subjected to various environment conditions and accelerated evaluations. Inasmuch as the increase in the resin melting point peaked at about 12° C., in some embodiments, this difference was incorporated into the initial design considerations for the integral indicator as shown above in Table 1A, where, for example, the melting point of such a resin should range from about 38-109° C., i.e., to adequately address $T_m$ changes pursuant to the molding process, aging, and exposure to variable environmental conditions, in illustrative embodiments.

Notwithstanding the foregoing, it will be readily apparent to the skilled artisan that, in addition to differing types and grades of resin materials, numerous additional variables can impact the melting point or temperature of the precursor resin materials and/or the polymeric materials of the integral indicators. As such, temperature increases or decreases, or the absence of any such variations, are envisaged with respect to the present methods. To this end, temperature differences ranging from about 0.1, 1, 5, 10, 50. 75, 100, or 150° C. to from about 1, 5, 10, 25, 50, 75, 100, 150, or 200° C. are within the scope of the present invention.

Along the same lines, and pursuant to ASTM 1238, it was determined that the melt flow rate of the molded resin, subsequent to storage and shipping conditions, i.e., via ECAA evaluative testing, should range from about 5-1000 g/10 minute. With respect to the resin precursor in this regard, the melt flow rate of the molded resins has been identified to increase per the molding process and/or the ECAA evaluations, in some embodiments, from about 0.1%, 1%, 5%, 10%, 15%, 25%, 30%, 40%, 50%, 75%, 80%, or 90% to from about 1%, 5%, 10%, 15%, 25%, 30%, 40%, 50%, 75%, 80%, 90%, 95%, or 99%, respectively. For example, when a 40% increase is observed pursuant to the molding process, and a 25% increase is identified in view of the ECAA testing, the resulting melt flow rate of the resin material should range about from 2.86-571 g/10 minutes, in illustrative embodiments.

After accounting for storage and shipping variables, the mechanical properties, i.e., tensile strength, tensile modulus, and strain-at-break, of the integral indicator should satisfy the design requirements recited above in Tables 1 and 1A. Nevertheless, because the tensile strength and elongation-at-break were, for example, determined to decrease by 50% upon ECAA evaluation, the mechanical design parameters recited in Table 1A should be employed, in some embodiments, to control for such variations, as necessary.

As such, the present methods of manufacturing an integral indicator include the steps of: (a) selecting a resin possessing a melting temperature ranging from about 38-109° C. and a melt flow rate ranging from about 2-600 g/10 minute, (b) selecting one or more medical device components, and (c) modifying the resin to form a solid polymeric material that is capable of being molded to the one or more medical device components as the integral indicator, where the polymeric material possesses a tensile strength ranging from about 20-400 MPa, a tensile modulus ranging from about 4-1000 GPa, and a strain-at-break ranging from about 4-1000%, and (d) where the integral indicator is configured to irreversibly transition from an operative conformation to an inoperative conformation in response to an exposure after the single-procedure.

Likewise, the method further entails the step of (e) determining the chemical and mechanical stability of the integral indicator after being subjected to one or more atmospheric conditioning steps and storage steps, or the equivalents thereof, in illustrative embodiments. In suitable embodiments, the integral indicator is chemically and mechanically stable when it possesses a melting temperature ranging from about 50-121° C., a melt flow rate ranging from about 5-1000 g/10 minute, a tensile strength ranging from about 10-200 MPa, a tensile modulus ranging from about 2-500 GPa, and a strain-at-break ranging from about 2-500%, following the one or more conditioning steps and storage steps, or equivalents thereof.

Along the same lines, the precursor resin, biocompatible thermoplastic polymers, polymeric materials, molded resin, and integral indicators disclosed herein possess chemical and mechanical properties that impart the required, temperature-dependent, state to function in accord with the aspects and embodiments disclosed herein. As such, in some embodiments, an integral indicator is manufactured from the polymeric materials and precursor resin, which possess a melting temperature ($T_m$) ranging from about 1-500° C., 5-300° C., 10-200° C., 25-175° C., 35-150° C., or 50-121° C. In suitable embodiments, the melting temperature ranges from about 50-121° C. Likewise, an integral indicator is manufactured from the polymeric materials and precursor resin, which possess a melt flow rate ranging from about 0.1-9000, 1-7,000, 2-5,000, 3-3,000, 4-2,000 or 5-1000 g/10 minute. In illustrative embodiments, the melt flow rate ranges from about 5-1000 g/10 minute.

Furthermore, the chemical and physical properties of the foregoing materials possess a tensile strength ranging from about 1-500, 3-400, 5-300, 7-250 or 10-200 MPa. In illustrative embodiments, an integral indicator is manufactured from the polymeric materials and precursor resin, which possess tensile strength ranging from about 10-200 MPa. An integral indicator is manufactured from the polymeric materials and precursor resin, which possess a tensile modulus, moreover, ranging from about 0.001-900, 0.01-800, 0.1-700, 1-600 or 2-500 GPa. In illustrative embodiments, the tensile modulus ranges from about 2-500 GPa. An integral indicator is manufactured from the polymeric materials and precursor resin, which possess a strain-at-break ranging from about 0.001-900, 0.01-800, 0.1-700, 1-600 or 2-500%. In illustrative embodiments, the strain-at-break ranges from about 2-500%.

In illustrative embodiments, the molded, solid, polymeric material formed from the precursor resin material possesses chemical and mechanical properties selected from a melting temperature ranging from about 50-121° C., a melt flow rate ranging from about 5-1000 g/10 minute, a tensile strength ranging from about 10-200 MPa, a tensile modulus ranging from about 2-500 GPa, and a strain-at-break ranging from about 2-500%, and combinations thereof.

Further in view of the foregoing material property requirements, and ranges pertaining thereto, the integral indicators and polymeric materials formed from the precursor resin materials are, in some embodiments, selected from, but are not limited to, one or more polyolefins, polyethylene, polyolefin copolymers, poly(ethylene-co-acetate), polyesters, poly(ethylene-co-acrylate), polycaprolactone and aliphatic homopolymers thereof, polyethers, polyethyleneoxide, fluoropolymers, polypropyleneoxide, olyisoprene, polyamide, polystyrene, polysulphone, polyoxymethylene, polycarbonate, polyvinyl chloride, and acrylnonitrile butadiene styrene, and filled embodiments thereof, and combinations thereof. As noted above, such single-use devices and instruments are designed to incorporate the indicators of the present invention as an integral feature, which accordingly imparts a unitary structure that is stable for medical use at room temperature, yet heat labile pursuant to an exposure.

The exposure, in this regard, entails subjecting the surgical device, including the integral indicator formed of the polymeric materials that are molded out of the precursor resins, to: (i) one or more steam sterilization cycles, or (ii) an average temperature sufficient to precipitate the irreversible transition, or both, in some embodiments. In certain embodiments, the exposure entails: (i) subjecting at least 20% of the total surface area of the integral indicator to one or more steam sterilization cycles, or (ii) subjecting the total volume of the integral indicator to an average temperature sufficient to precipitate the irreversible transition, or both.

Concerning the heat energy of an exposure in concert with the melting temperature of the integral indicator formed of the polymeric materials that are molded out of the precursor resins, it is important in certain embodiments to consider the extent of device—and specifically, the integral indicator-surface area and volume that will be subjected to the elevated temperatures of such an exposure. More specifically, the integral indicator must be availed to a minimum threshold of localized temperature, for an amount of time, sufficient to achieve the irreversible transition. In some embodiments, the temperature range and duration of an exposure is modified based on the presence of one or more single-procedure device insulator materials.

Integral indicator embodiment variations, in this regard, include insulated portions or regions of the device or integrated indicator, or both, which consequently impacts the temperature range and duration of an exposure required to precipitate the irreversible transition from the surgically operable conformation to the surgically inoperable conformation, in some embodiments. In this respect, the integrally incorporated indicator device typically possesses a structural conformation that is heat-accessible pursuant to an exposure, i.e., such that the energy, in the form of heat, is transferred to the polymeric materials of the integral indicator. This energy transfer, e.g., in the form of heated water or steam, occurs via direct transference or contact with the surface area of the integral indicator, in some embodiments. The elevated temperatures of an exposure, in other embodiments, e.g., such as when an insulator is present, may access or transfer to the polymeric materials of the integral indicator through conduction via a metal conduit.

In some embodiments, both surface area contact and conducted heat transfer occur to precipitate the irreversible transition of the integral indicator from the operable conformation or configuration to the inoperable conformation or configuration. As such, these design considerations should be accounted for when incorporating the integral indicator into the medical device. With respect to the conductance of heat transferred through a suitable metal conduit, such a mechanism may not be required to the extent that the integral indicators of the present invention are not enveloped or contacted by an insulator.

Insofar as such insulator materials are present and accordingly provide at least a measure of protection from the exposure, heat conductance transfer may be require to morphologically impart the irreversible transition to the inoperable conformation. As such, when manufacturing the indicators that are integral to the single-procedure devices of the present technology, the foregoing spacial and local relative positioning considerations should be taken into consideration.

As such, in some embodiments, the following design indications are critical considerations for the development and manufacture of the present integral indicators: (i) possessing a minimal volume and/or surface region subjected to the exposure, and (ii) possessing an area sufficient to allow for the melted polymeric material to flow away from its local position, where, in the absence of possessing such an area, the melted polymeric material may retained its shape and re-solidify following the exposure.

In accord with the device and system descriptions above, the methods of the present disclosure include medical device components, in some embodiments, where, in such embodiments, the components entail one or more non-indicator domains that: (i) are not composed of the resin or the polymeric material, or (ii) remain in the operative conformation in response to the exposure, or the combination of both (i) and (ii). In illustrative embodiments, the one or more non-indicator domains are composed of one or more materials selected from metals, metal alloys, shape memory alloys, titanium, nickel, copper, plastics, polymers, ceramic materials, composite materials, and stainless steel, and combinations thereof.

Likewise, such non-indicator domains, when present, function to facilitate the various material preconditions that may pertain to certain medical devices, including single-procedure devices of the present invention, which are designed to incorporate an integral indicator as detailed herein. In suitable embodiments, non-limiting examples of the one or more non-indicator domains include the distal end or region of the device, the surgically functional domain of the device, one or more shaft or conduit regions, and/or certain portions of the proximal end or region of the device, but only insofar as an integral indicator is not already locally occupying, or intended to occupy, such an end, region or domain.

Nevertheless, the single-procedure surgical or medical device, in suitable embodiments, possess one or more precursor resin materials selected from, but not limited to, one or more of the various grades and types of Capa™ or Elvax®, or both. While such biocompatible resin compositions are employed with respect to the present technology, in suitable embodiments, substantially similar compositions may be used in certain embodiments. Such substantially similar compositions include, but are not limited to, e.g., related molecules, materials, compounds, polymers, and compositions possessing a similar or identical functional and/or structural profile or are coterminous with the physical propertied of the compositions used herein.

With respect to the material compositions and related properties, characteristics or parameters, which allow for a substantially similar or identical integral indicator to be manufactured, these compositions are also acceptable in suitable embodiments. Likewise, the present disclosure contemplates one or more structures, conjugates, compounds, compositions and the like, consistent with the absorbance profile, molecular and/or steric profiles, conformation, structural and/or empirical formulations, stoichiometric ratios, spectrophotometric profiles, NMR profiles, refractive indices, liquid transition temperatures, and/or other data profiles consistent with the present compositions.

In view of the foregoing, it has been determined that the melting behavior, thermal transition characteristics, chemical constitution, and mechanical properties of the integral indicators and polymeric materials composed of the precursor resin materials, such as, for example, but not limited to, polycaprolactone and poly(ethylene-co-vinyl acetate), are critical chemical and material properties in the development and design of single-procedure devices possessing integral indicators, in illustrative embodiments.

Furthermore, to this end, it was determined, in suitable embodiments, that: (i) the crystalline properties of the resin changed after being subjected to the molding process, which indicates that such process parameters influence the molecular arrangement and corresponding mechanical properties, (ii) there is a directly proportional dependence relating to the tensile properties of the molded integral indicator and the molecular weight of the polymeric materials, (iii) the chemical constitution of the molded polymeric materials remained static when subjected to ECAA evaluations, and (iv) the melting point increased, while the mechanical property values decreased when the materials were subjected to ECAA evaluations.

FIG. 1 shows an illustrative embodiment of an operation 100 concerning the present invention. In an operation 110, a control medical device composed of a proximal end 120, conduit region 130, and distal end 140 is provided. In operation 150, the proximal end contains integral indicator 160, prior to being subjected to an exposure, such as, but not limited to, a steam sterilization cycle. After the medical device containing the integral indicator is subjected to such an exposure, in operation 170, the proximal end containing the integral indicator 180 melts away thereby rendering the device inoperable and incapable of any further use. As can be seen in operation 170, the conduit region 130 and distal end 140, remain intact.

EXAMPLES

The present integral indicators, devices, systems, compositions, and methods will be understood more readily by reference to the following examples, which are provided by way of illustration and are not intended to be limiting in any way.

Example 1—Preparation, Selection, and ECAA Parameters Relating to the Integral Indicator Polymeric Materials Materials.

Thermoplastic polymers were determined to be suitable polymeric materials inasmuch as they can be conformed or configured into device components of any desired specification via melt-processing techniques, such as, but not limited to, molding, extrusion, etc. The molecular weight of the polymeric materials was also determined to be a crucial aspect for the intended application at least because of its relationship with, and influence on, the mechanical properties, e.g., tensile strength, tensile modulus, and elongation at break, as well as the viscosity of melt, of the integral indicator component.

Figure 2:
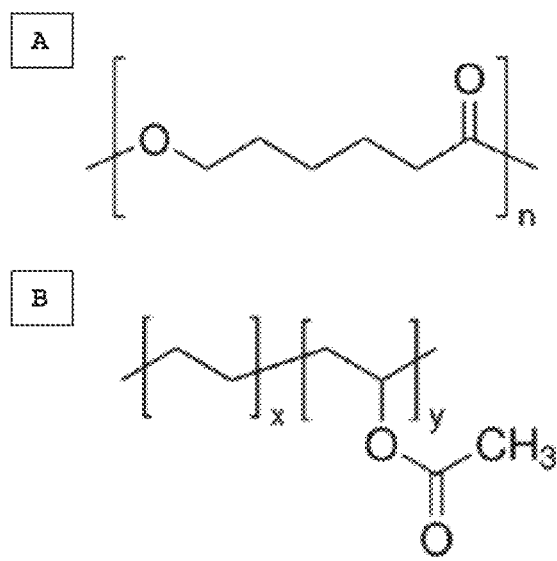
FIGS. 2A-2B show the respective molecular structures for the selected Capa™ and Elvax® polymeric materials.

Two polymeric materials were initially selected for material and chemical evaluation as follows: polycaprolactone or Capa™ (Perstrop, Orgnr. Malmö, Sweden) and poly(ethylene-co-vinyl acetate) or Elvax® (DuPont, Inc., Wilmington, Del.). Polycaprolactone resin (Capa™ 6500), which has an average molecular weight (MW) of 50 kDa, and Capa™ 6250 having an average MW of 25 kDa, were initially selected. Both Capa™ polymers possess melting point ($T_m$) between 58-60° C. Insofar as poly(ethylene-co-vinyl acetate) is a co-polymer, the ratio of the combined polymers also contributes to the melt flow property. Three different grades of Elvax® were initially selected: (i) Elvax® 250, which has a 28 percent by weight (wt %) of vinyl acetate, a melt flow index of 25 g/10 min., and a $T_m$ of 70° C.; (ii) Elvax® 420, which has a 18 wt % of vinyl acetate, a melt flow index of 150 g/10 min., and a $T_m$ of 73° C.; and (iii) Elvax® 410, which has a 18 wt % of vinyl acetate, a melt flow index of 500 g/10 min., and a $T_m$ of 73° C., as distributed by Univar USA (Downers Grove, Ill.). The Capa™ and Elvax® molecular structures are respectively shown in FIGS. 2A-2B.

Environmental Conditioning and Accelerated Aging (ECAA).

As further detailed below, the chemical constitution, crystallization behavior, and mechanical properties, of the polymeric materials of the present invention, were subjected to various atmospheric conditions, pursuant to ISTA (International Safe Transit Association) Standard 2A for Atmospheric Conditioning, and additionally subjected to accelerated aging (ASTM F1980) in various examples below. In this regard, it was determined that the chemical composition of the polymeric materials remained the same, but the melting point, however, was shown to increase, while the mechanical property values of the polymeric materials decreased when subjected to ECAA evaluation, which was equivalent to one year at ambient conditions. See also Example 7.

Example 2—Polymeric Material Evaluation

The different grades of the Capa™ and Elvax® polymeric materials were evaluated to ascertain the resin melting behavior in concert with the corresponding molded integral indicator component via oven heating and Differential Scanning Calorimetry (DSC). The molecular structure of the molded components and resin, moreover, were investigated by Fourier Transform Infrared (FTIR) Spectroscopy. The mechanical properties, i.e., shore hardness, tensile strength, and strain-at-break, of the resin and molded indicator components were also examined. Furthermore, the polymeric material molds were subjected to environmental/atmospheric conditioning pursuant to ISTA Standard 2A for Atmospheric Conditioning, while subsequently subjected to accelerated aging (ASTM F1980), as follows.

Figure 3:
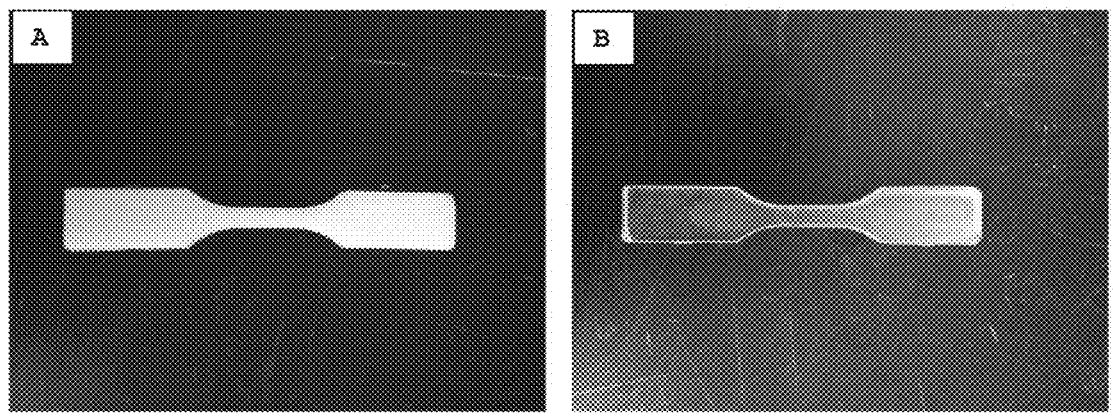
FIGS. 3A-3B are photographs of the selected Capa™ and Elvax® polymeric materials, respectively, subsequent to twin screw injection molding.
Figure 4:
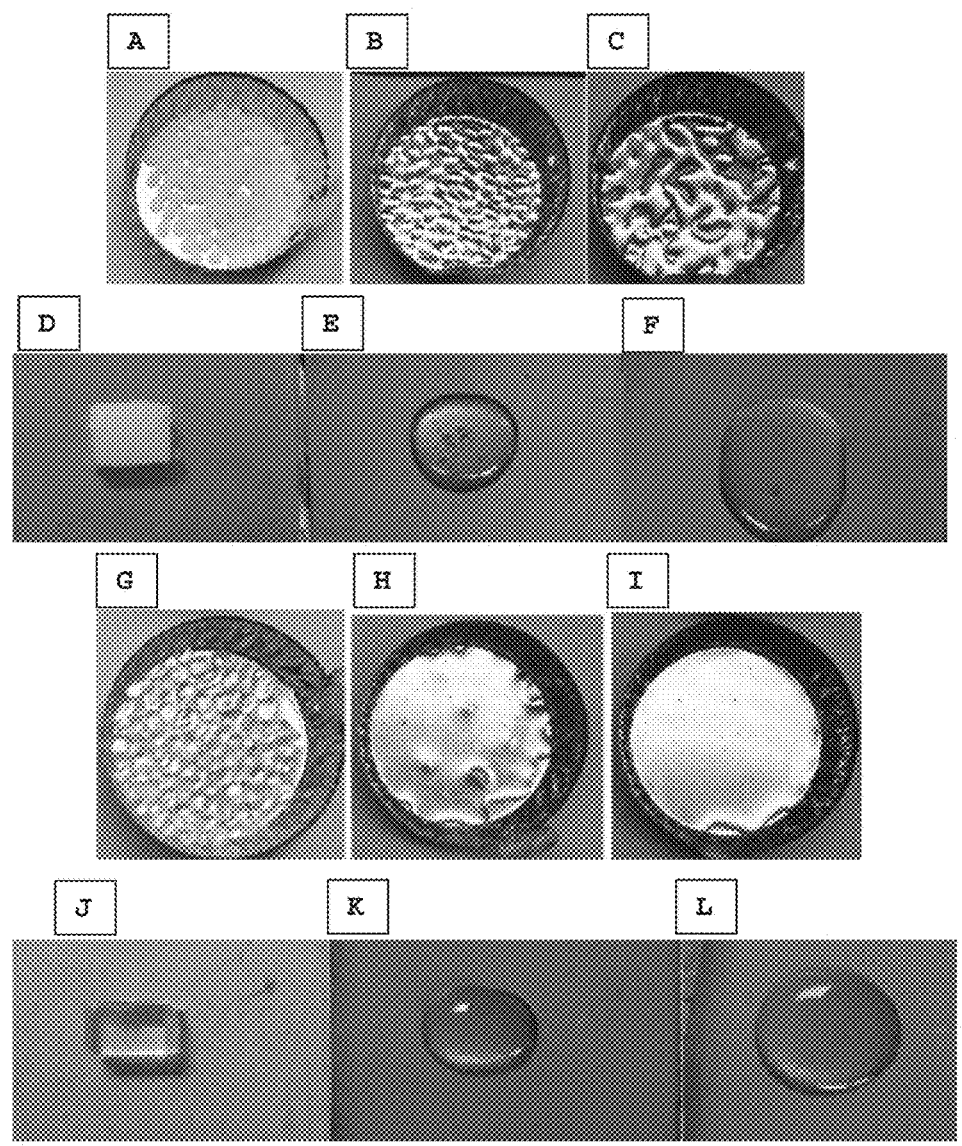
FIGS. 4A-4L are photographs of Capa™ and Elvax® pellets and molded barbell components after high temperature incubations.

The components in this regard were initially molded into a "dog-bone" or barbell shape, which possesses dimensions corresponding to Sample Type V presented in the ASTM Standard D638-14. See ASTM D638-14, "Standard Test Method for Tensile Properties of Plastics," *ASTM International*, West Conshohocken, Pa. (2014). The molding was conducted using a twin screw injection machine. See FIGS. 3A-3B (Capa™ and Elvax® respectively).

Example 3—Physical and Mechanical Properties of the Molded Polymeric Materials

Melting Behavior (Oven Heated).

Oven-heated melting analyses were performed on each of the molded polymeric materials indicated above, where various types of Capa™ pellets (see FIG. 4A-4C) and barbell molds (see FIG. 4D-4F), and, separately, the above noted grades of Elvax® pellets (see FIG. 4G-4I) and barbell molds (see FIG. 4J-4L), were subjected to time and temperatures cycles similar to typical autoclave steam sterilization cycle, e.g., 134° C. for 3 and 18 minutes. The results show that, in each case, the polymeric materials melted into a flow-able liquid. Specifically, FIGS. 4A-4L show photographs of molded Capa™ pellets (FIGS. 4A-4C) and Capa™ barbell mold portions (FIG. 4D-4F), subjected to 3 min. of 134° C. temperature (FIGS. 4B and 4E), 18 min. of 134° C. temperature (FIGS. 4C and 4F), and Capa™ controls (FIGS. 4A and 4D), while molded grades of Elvax® pellets (FIGS. 4G-4I) and Elvax® barbell mold portions (FIG. 4J-4L), were also subjected to 3 min. of 134° C. temperature (FIGS. 4H and 4K), 18 min. of 134° C. temperature (FIGS. 4I and 4L), and Elvax® controls (FIGS. 4G and 4J) as shown.

Example 4—Indicator Thermal Transition Properties

Differential Scanning.

Figure 5:
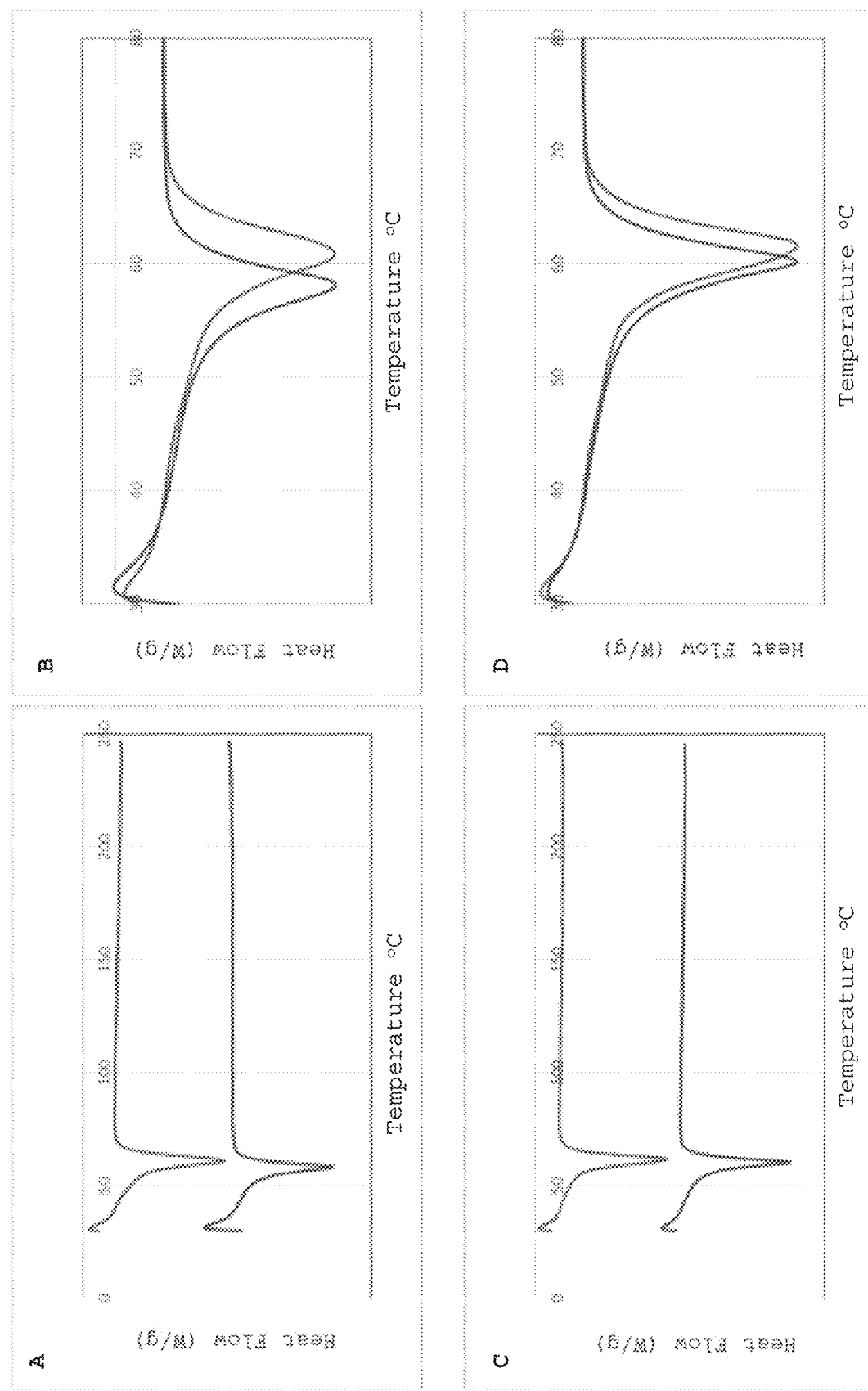
FIGS. 5A-5D are graphic representations of Capa™ Differential Scanning Calorimetric (DSC) plots.

Calorimetric plots are shown as graphic representations of Capa™ using Differential Scanning Calorimetry (DSC). See FIGS. 5A-5D. FIG. 5A is a DSC of Capa™ 6500 pellet and barbell molded components, while FIG. 5B shows narrower ordinate-abscissa parameters centered on the melt transition inflection points. FIG. 5C is a DSC of Capa™ 6250 pellet and barbell molded components, while FIG. 5D shows narrower ordinate-abscissa parameters centered on the melt transition inflection points.

Figure 6:
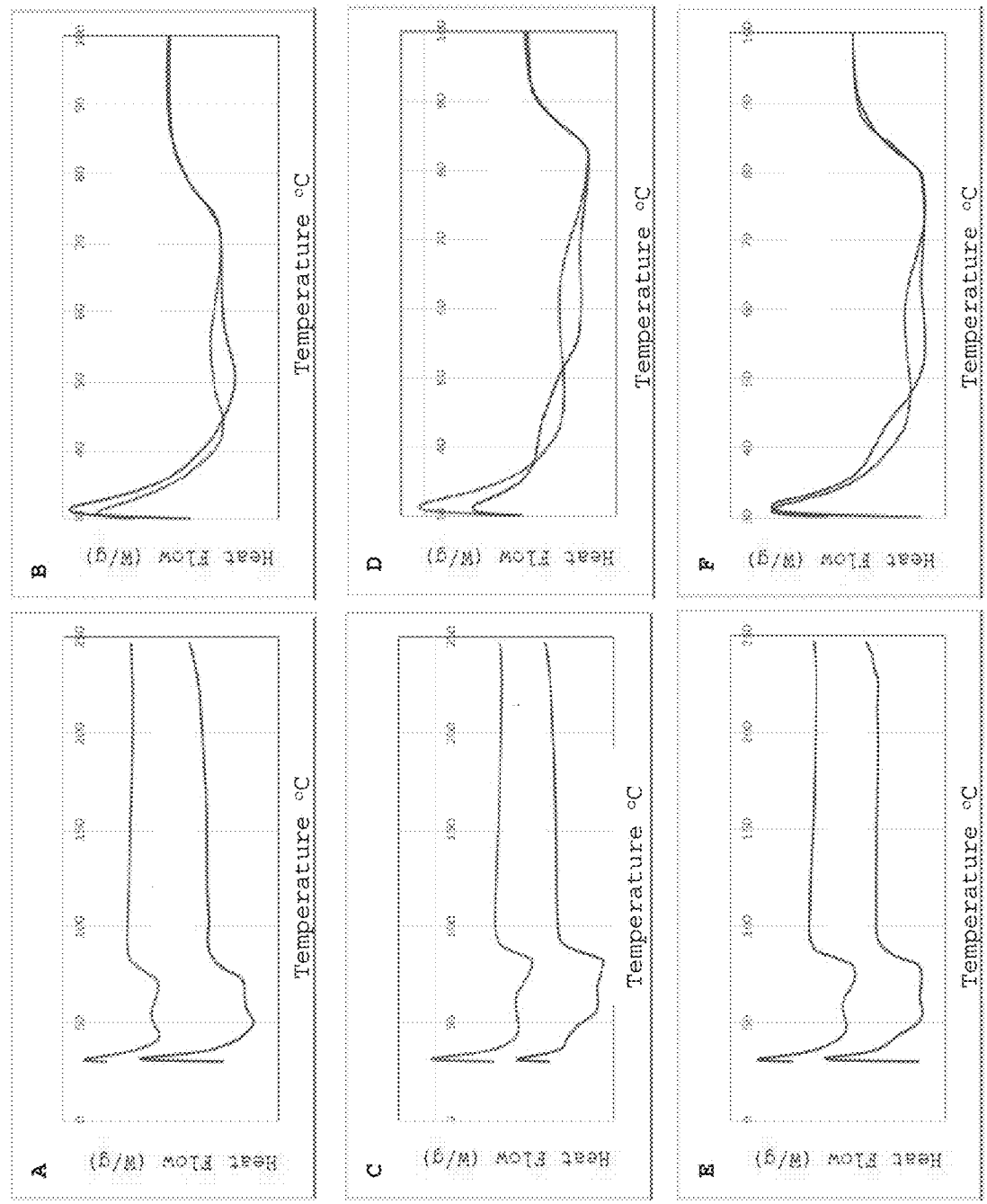
FIGS. 6A-6F are graphic representations of Elvax® Differential Scanning Calorimetric (DSC) plots.

Calorimetry plots are shown as graphic representations of Elvax® using Differential Scanning Calorimetry (DSC). See FIGS. 6A-6F. FIG. 6A is a DSC of Elvax® 250 pellet and barbell molded components, while FIG. 6B shows narrower ordinate-abscissa parameters centered on the melt transition inflection points. FIG. 6C is a DSC of Elvax® 420 pellet and barbell molded components, while FIG. 6D shows narrower ordinate-abscissa parameters centered on the melt transition inflection points. FIG. 6E is a DSC of Elvax® 410 pellet and barbell molded components, while FIG. 6F shows narrower ordinate-abscissa parameters centered on the melt transition inflection points.

The melting characteristics and corresponding physical properties were compared between the polymeric material pellets and barbell components of the integral indicator for each type and grade of the polymeric materials. As noted above, FIGS. 5A-5D and FIGS. 6A-6F show the DSC plots of the two types of Capa™ polymers and three grades of Elvax® polymer, respectively, where, for each polymer type and grade, the temperature-heat flow relation between the pellet and the barbell mold is compared. Pursuant to FIGS. 5A-4D, the following thermal characteristic properties of the Capa™ polymers were ascertained as present in Table 3 below.

TABLE 3

| Capa ™ Type | Physical/Molded Form | Melting Point | Heat of Melting |
|---|---|---|---|
| Capa ™ 6500 | Pellet | 58.2° C. | 65.2 J/g |
| Capa ™ 6500 | Barbell | 60.7° C. | 72.8 J/g |
| Capa ™ 6250 | Pellet | 59.7° C. | 82.6 J/g |
| Capa ™ 6250 | Barbell | 61.2° C. | 85.5 J/g |

The Table 3 data indicate that there is an increase in the melting point, and heat of melting, for both types of Capa™ upon molding into the barbell structure. An increase in crystallite size imparts the increase in the melting point, while the increase in heat of melting connotes that the degree of crystallinity in the barbell molded component occurs to a greater relative extent.

The melting transition properties identified with respect to the tested Elvax® polymeric materials occurs over an increased temperature range compared to the Capa™ polymeric materials. Moreover, multiple local minima were observed for each grade and form of the Elvax® polymeric materials. Such characteristics indicate the likelihood of overlapping peaks due to an expansive distribution range with respect to the molded component crystallite size. In view of FIGS. 6B, 6D, and 6F, it is determined that the melting transitions are comparable between the polymeric material pellets and barbell molds, where the local minimum for the higher temperature peaks were essentially identical.

Example 5—Indicator Chemical and Molecular Properties

Spectroscopy.

Figure 7:
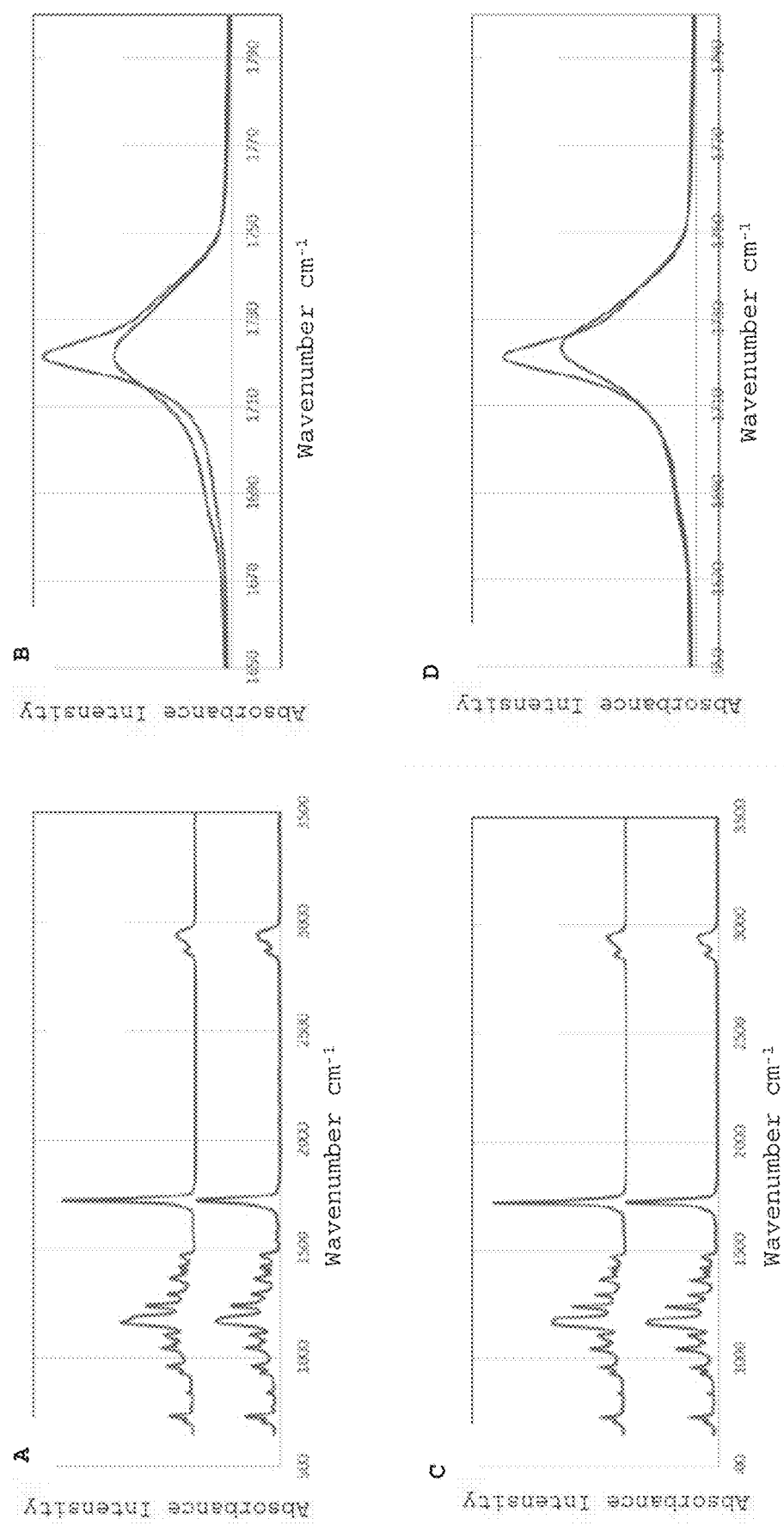
FIGS. 7A-7D are graphic representations of Fourier Transform Infrared (FTIR) spectroscopic analyses.
Figure 8:
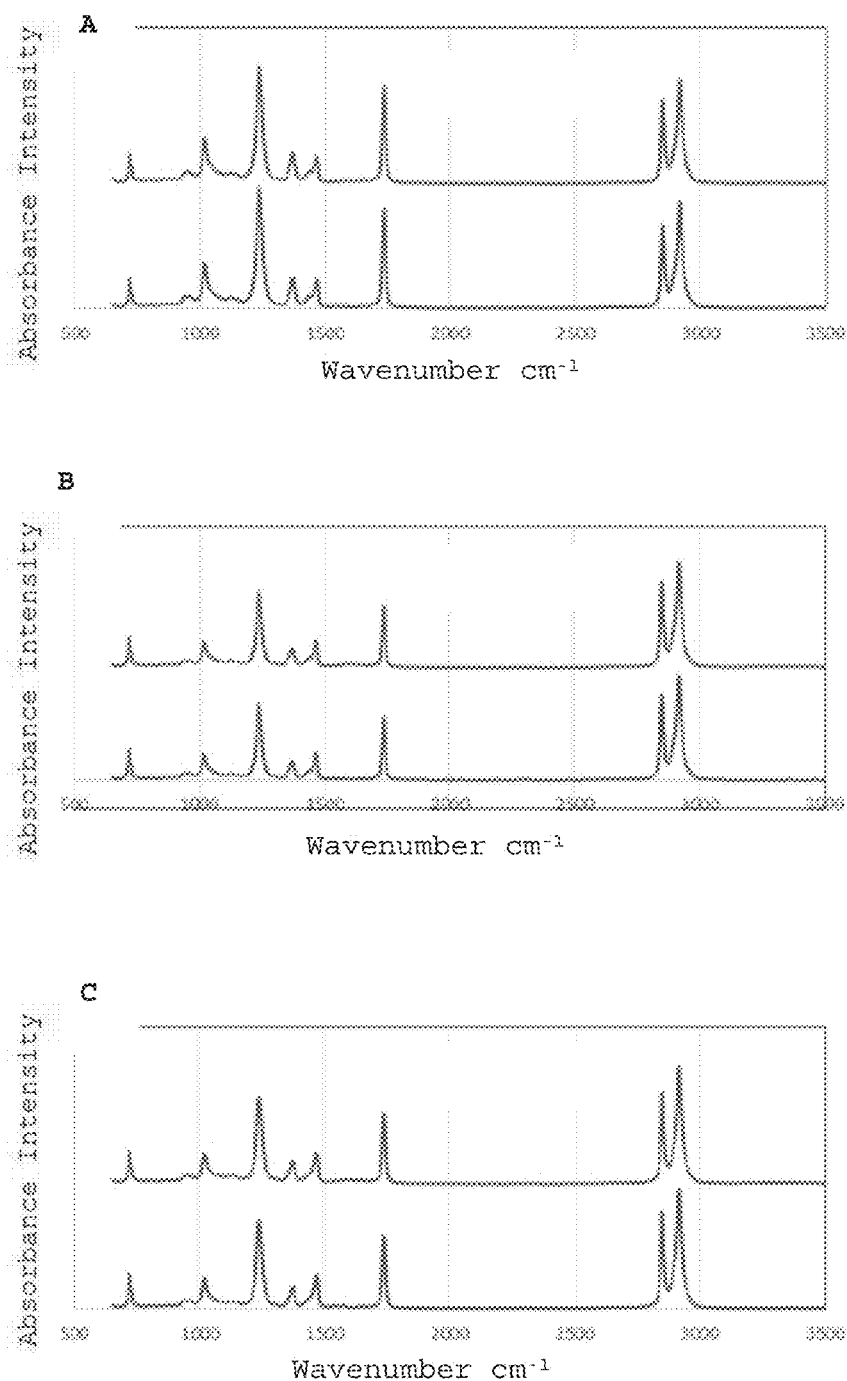
FIGS. 8A-8C are graphic representations of Fourier Transform Infrared (FTIR) spectroscopic analyses.

Fourier Transform Infrared (FTIR) spectroscopy was employed to reveal the chemical composition of the polymeric materials. The prominent FTIR spectroscopy peak wavenumbers for Capa™ were determined as 2920-2950 $cm^{-1}$ and 2845-2875 $cm^{-1}$ for $CH_2$ asymmetric and symmetric vibrational stretching, respectively, while 1170 $cm^{-1}$ was identified for asymmetric C—O—C vibrational stretching, and 1710-1750 $cm^{-1}$ for C=O vibrational stretching. See FIGS. 7A-7D. The poly-caprolactone carbonyl band consisted of two components, a crystalline band at 1724 $cm^{-1}$ and an amorphous band at 1737 $cm^{-1}$, but nevertheless appeared as a single peak due to their overlapping profile. See FIGS. 7B and 7D. The pellet and barbell FTIR spectra appear identical except to the extent that for both Capa™ 6500 and Capa™ 6250 the crystalline band is more prominent for the molded barbell. As such, FTIR spectroscopy demonstrates that the Capa™ polymeric material results are in accord with the DSC analysis discussed above.

The FTIR spectroscopy of the Elvax® polymeric materials indicate identical peaks for both the pellet and barbell components with respect to each grade tested. This data confirms that there was no change in the chemical composition or molecular structure for the tested materials. FTIR spectrum bands assigned to vinyl acetate were 1740 $cm^{-1}$ (C=O vibrational stretching), 1240 $cm^{-1}$ (asymmetric C—O vibrational stretching) and 1020 $cm^{-1}$ (symmetric C—O vibrational stretching). FTIR spectrum bands assigned to ethylene were 2920 $cm^{-1}$, where 2850 $cm^{-1}$ relates to the $CH_2$ vibrational stretching. As can be seen for Elvax® 250, which contains an increased concentration of vinyl acetate, the C=O vibrational stretching peaks are prominent.

Example 6—Indicator Mechanical Properties

Figure 9:
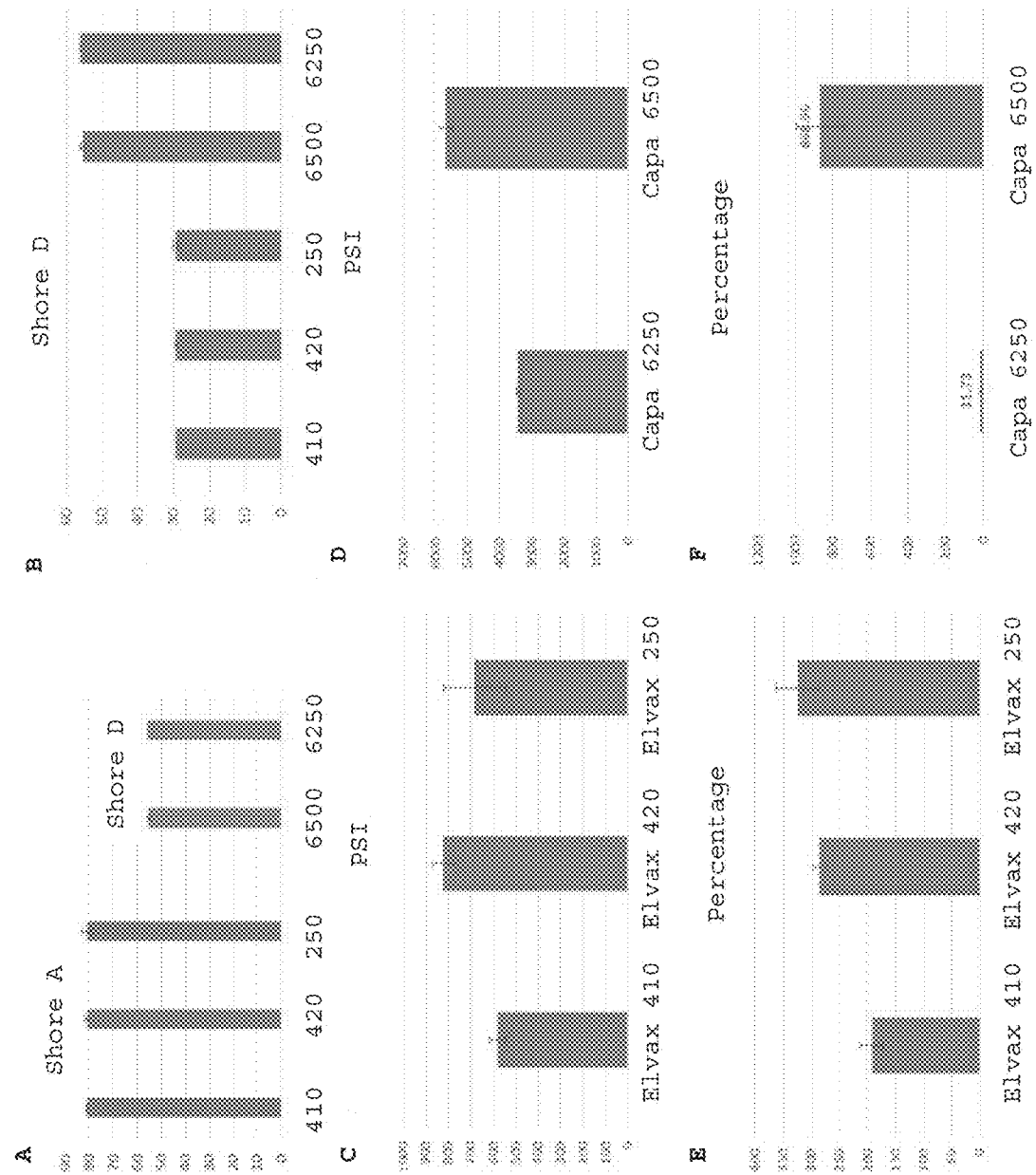
FIGS. 9A-9F are graphic representations of the evaluated polymeric materials and their associated mechanical properties.

As detailed above and herein, the hardness, tensile strength and the strain-at-break were determined for the selected polymeric materials. The evaluated Elvax® molded barbells possessed relatively softer properties than the Capa™ barbells, which imparted the disparate techniques relating thereto, i.e., Shore A and Shore D were employed to measure hardness as shown in FIG. 9A. The hardness values among the Elvax® grades, and between the Capa™ types are comparable. Upon normalization of the hardness values (FIG. 9B), it can be seen that the hardness of the Capa™ components is approximately twice as great as the Elvax® pellets.

The tensile strength range of the Elvax® components was approximately 500-800 psi, as detailed in FIG. 9C. When comparing Elvax® 410 and Elvax® 420, which possess identical vinyl acetate content, the results indicate that the tensile strength is higher for the grade with possessing a lower melt flow rate, which accordingly has a higher molecular weight. The tensile strength of Capa™ barbells was between 3000-6000 psi, which is about six-fold greater than the Elvax® components. See FIG. 9D. The tensile strength of Capa™ 6500 was found to be greater than Capa™ 6250, which, in accord with the data above, possesses a lower relative molecular weight. The strain-at-break for the evaluated Elvax® barbells was comparable for all Elvax® grads, i.e., approximately ranging from 150-400 psi, as shown in FIG. 9E.

The strain-at-break, moreover, for Elvax® 420 was greater than Elvax® 410, again demonstrating a directly proportional relationship with the molecular weight of the tested polymeric material. FIG. 9F depicts the strain-at-break values for Capa™ 6250, which was markedly lower than Capa™ 6500, i.e., about 75 fold, and thus indicates that molecular weight imparts a more dynamic relationship with respect to strain-at-break for Capa™ materials compared to Elvax®.

Example 7—Environmental Conditioning and Accelerated Aging

Atmospheric Conditioning.

The environmental conditioning test was based on ISTA Standard 2A, where, for the present evaluations, the barbell components were subjected to a sequence of conditions as outlined in Table 4 below.

TABLE 4

| Atmospheric Conditions | Temp. (° C.) | Rel. Humidity | Time in Hours (minimum) |
|---|---|---|---|
| Step 1 (stnd) | 23 ± 5 | 50 ± 10% | 6 |
| Step 2 (frozen/winter) | −29 ± 2 | uncontrolled | 72 |
| Step 3 (tropical/wet) | 38 ± 2 | 85 ± 5% | 72 |
| Step 4 (desert/dry) | 60 ± 2 | 30 ± 5% | 6 |
| Step 5 (stnd) | 23 ± 5 | 50 ± 10% | 6 |

Accelerated Aging.

The accelerated aging test was based on ASTM F1980, "Standard Guide for Accelerated Aging of Sterile Medical Device Packages," as detailed above. The test parameters are governed pursuant to the $Q_{10}$ thermodynamic temperature coefficient, i.e., the Arrhenius equation, where a rise in temperature of 10° C. will approximately double the rate of a given chemical reaction. Here, AAR (Accelerated Aging Rate)=$Q_{10}^{((Te-Ta)/10)}$, where $T_a$ is the ambient temperature in Celsius, $T_a$ is the elevated temperature, and $Q_{10}$ represent a the reaction rate of 2. Moreover, AATD (Accelerated Aging Time Duration) is equivalent to the Desired Real Time/AAR.

Figure 10:
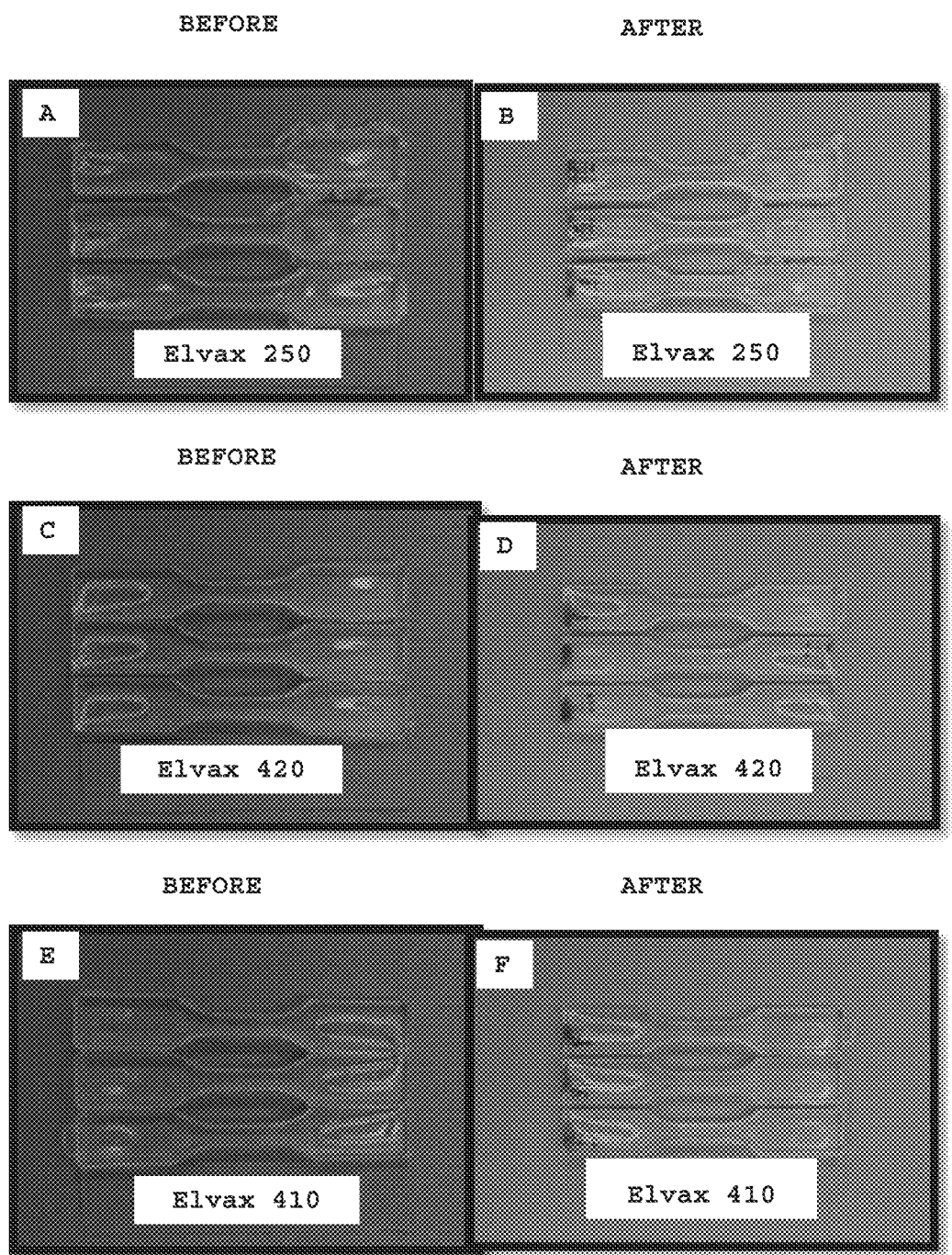
FIGS. 10A-10F are photographic representations of the evaluated Elvax® polymeric materials prior to and after being subjected to environmental conditioning and accelerated aging (ECAA).
Figure 11:
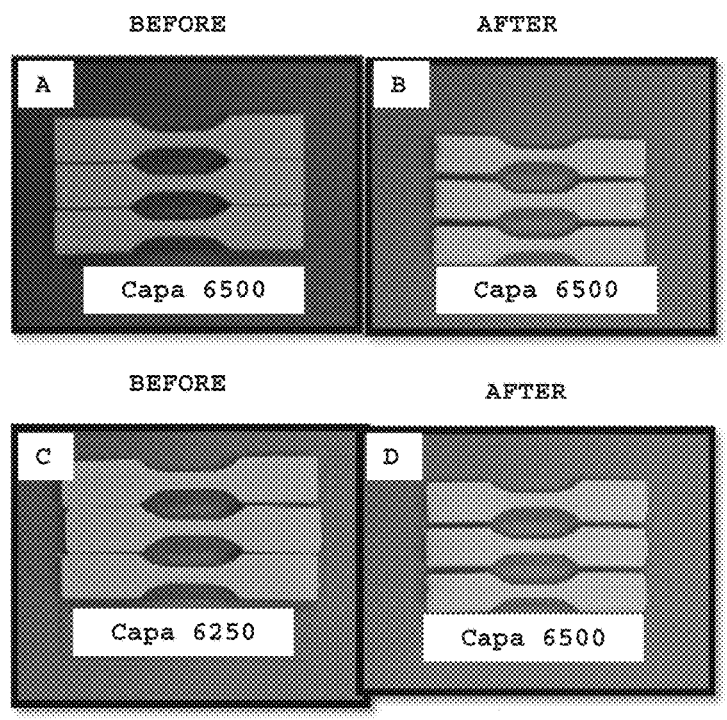
FIGS. 11A-11D are photographic representations of the evaluated Capa™ barbell polymeric materials prior to and after being subjected to environmental conditioning and accelerated aging (ECAA).

The Accelerated aging conditions were performed as follows, where the elevated temperature was 55° C. and the ambient temperature was 20° C. Along these lines, and for a Desired Real Time of 1 year, the Accelerated Aging Time Duration performed was 4.6 weeks. As shown in FIGS. 10-11, no ascertainable distinction was visualized after ECAA tests relating to the pellet barbells of pellets.

FTIR Spectra.

Figure 12:
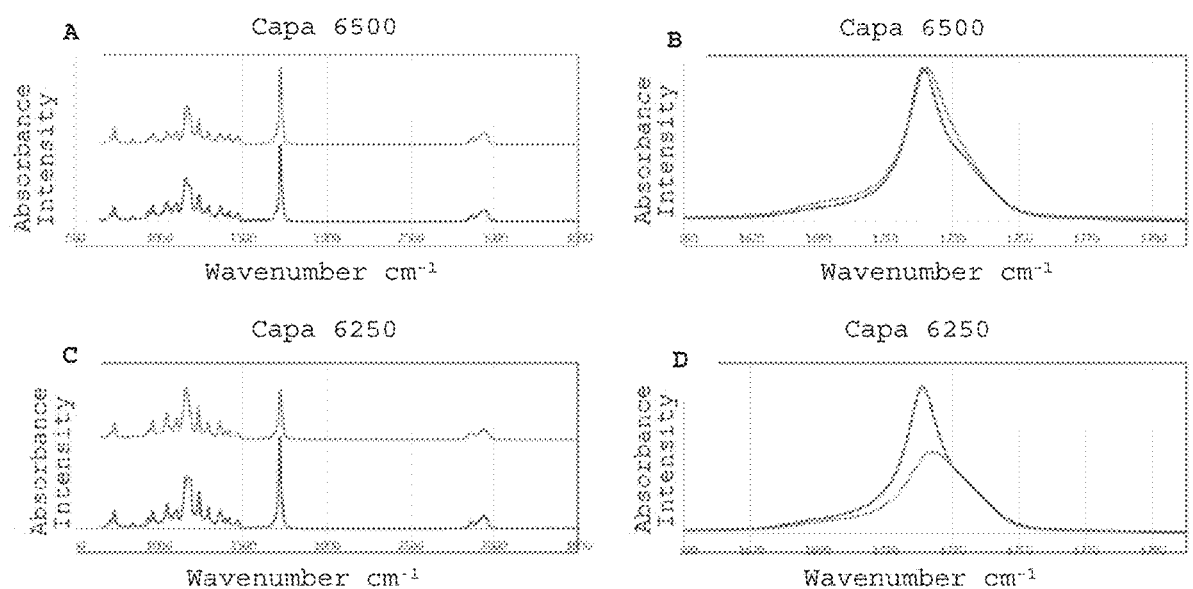
FIGS. 12A-12D present FTIR spectra for the Capa™ barbell polymeric materials prior to and after being subjected to environmental conditioning and accelerated aging (ECAA).

The FTIR spectra of Capa™ 6500 barbell components prior to and after environmental conditioning and accelerated aging are respectively shown in FIGS. 12A-12B, where FIG. 12B is an enlarged section of the spectra graph that focuses on the carbonyl band data. The FTIR spectra of Capa™ 6250 barbell components prior to and after environmental conditioning and accelerated aging are respectively shown in FIGS. 12C-12D, where FIG. 12D is an enlarged section of the spectra graph that focuses on the carbonyl band results. It can be seen from FIG. 12 that the FTIR spectra of the barbell components prior to and after environmental conditioning and accelerated aging test are identical for both Capa™ 6500 and Capa™ 6250, except to the extent that the crystalline band is less prominent for the Capa™ 6250 barbell components after environmental conditioning and accelerated aging test.

Figure 13:
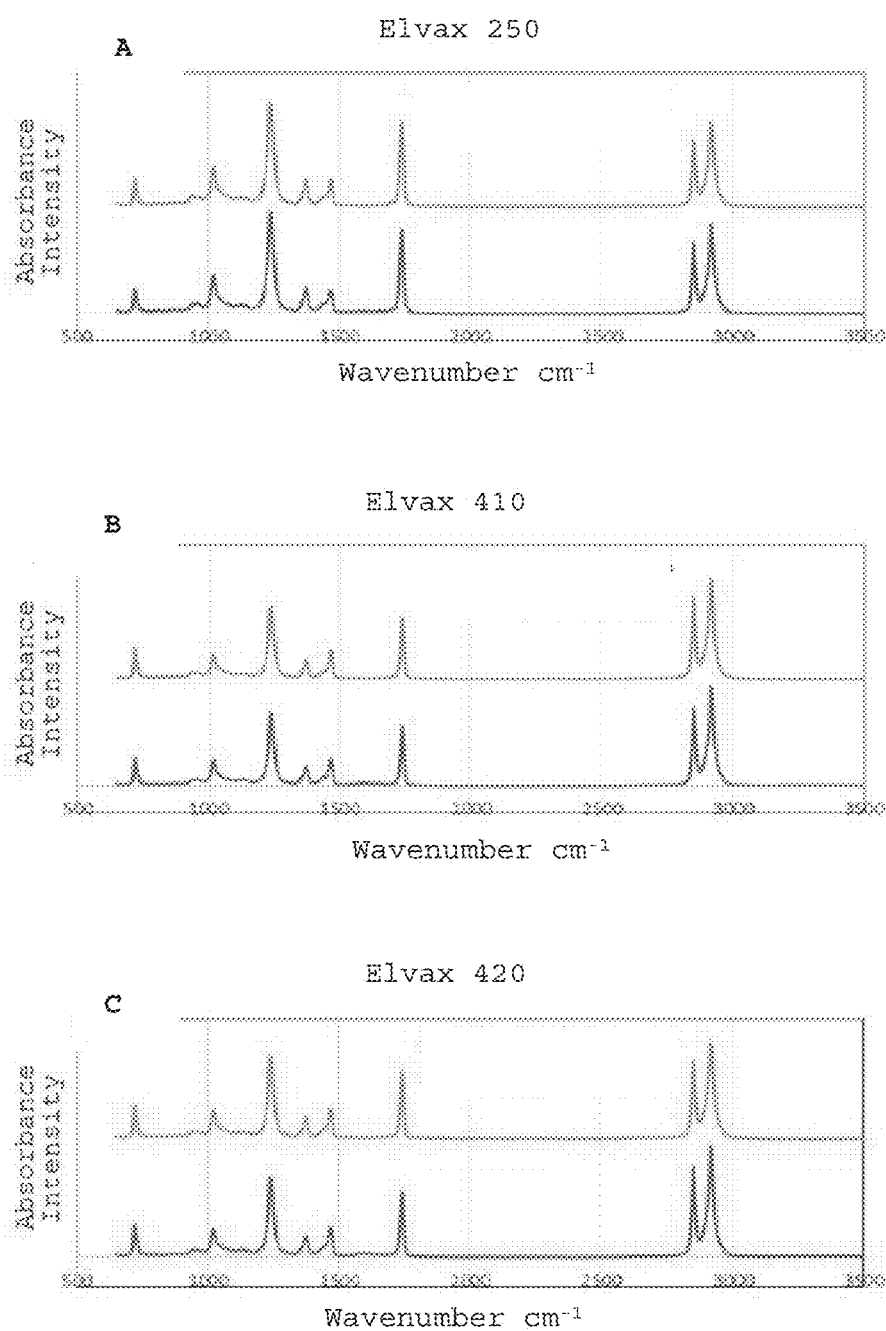
FIGS. 13A-13C show the FTIR spectra of Elvax® 250, Elvax® 410, and Elvax® 420 barbell molded components, respectively, prior to and after environmental conditioning and accelerated aging (ECAA). Regarding the forgoing spectra, the lower curve relates to barbell components prior to ECAA testing, while the upper curve concerns the barbell components after ECAA testing.

The FTIR spectra of Elvax® 250, Elvax® 410, and Elvax® 420 barbell components are respectively shown in FIGS. 13A-13C prior to and after environmental conditioning and accelerated aging. Regarding the forgoing evaluations, the lower curve relates to barbell components prior to the ECAA test, while the upper curve concerns the barbell components after ECAA testing. The FTIR spectroscopic results for the Elvax® polymeric materials indicates identical peaks for the barbell component prior to and after environmental conditioning and accelerated aging for each of the three Elvax® grades, and accordingly confirmed the absence of chemical and molecular structure transformations.

Example 8—Environmental Conditioning and Accelerated Aging Thermal Analyses

Differential Scanning.

Figure 14:
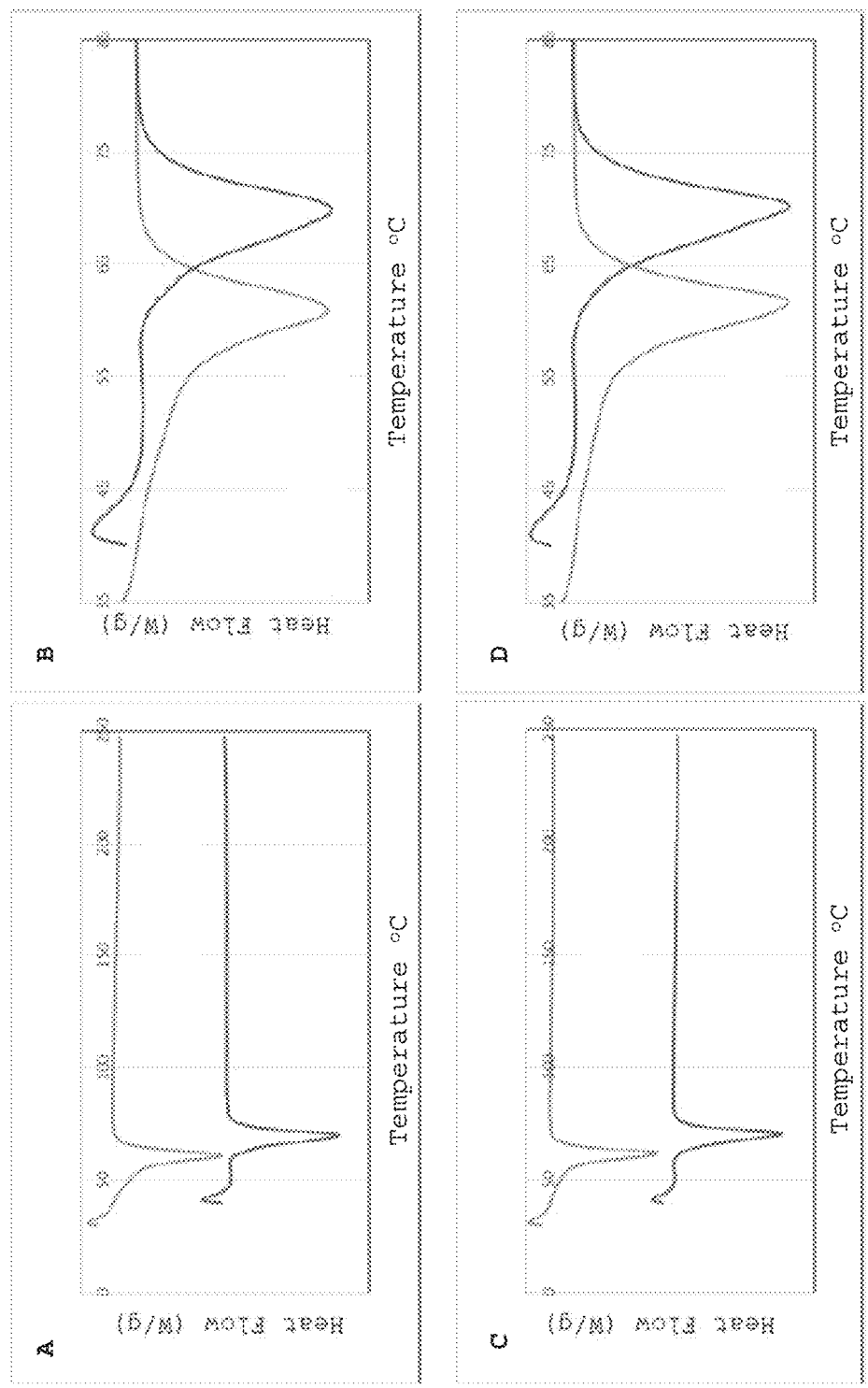
FIGS. 14A-14D are calorimetric plots as graphic representations of the Capa™ polymeric materials via Differential Scanning Calorimetry (DSC). The DSC plots for the barbell components of Capa™ 6500 and Capa™ 6250 are respectively shown in FIGS. 14A and 14C prior to and after environmental conditioning and accelerated aging (ECAA).

Calorimetry plots are shown as graphic representations of Capa™ using Differential Scanning Calorimetry (DSC). See FIGS. 14A-14D. The DSC plots for the barbell components of Capa™ 6500 and Capa™ 6250 are respectively shown as FIGS. 14A and 14C prior to and after environmental conditioning and accelerated aging. FIGS. 14B and 14D respectively show an enlarged section of the Capa™ 6500 and Capa™ 6250 DSC plots that highlight the melt transition inflection points. In concert with the melting characteristics, the corresponding physical properties were compared between the polymeric barbell components prior to and after ECAA testing. As noted above, FIG. 14 presents DSC plots regarding the Capa™ polymeric materials. For each type and condition of the Capa™ components, the following thermal characteristic properties were determined as shown below in Table 5.

TABLE 5

| Capa ™ Type | ECAA Testing | Melting Point. | Heat of Melting |
| --- | --- | --- | --- |
| Capa ™ 6500 | Prior | 60.7° C. | 72.8 J/g |
| Capa ™ 6500 | After | 69.8° C. | 69.0 J/g |
| Capa ™ 6250 | Prior | 61.2° C. | 85.5 J/g |
| Capa ™ 6250 | After | 69.5° C. | 78.7 J/g |

The data in Table 5 indicates that there is an increase in the melting point for both types of Capa™ upon being subjected to the ECAA parameters. Such an increase in the melting point emanates from an increase in crystallite size. And, as such, the foregoing results denote that there was a marked increase in the crystallite size, which imparted an approximate 9° C. increase in melting point. The heat of melting nevertheless decreased to a certain extent for Capa™ 6500 compared to Capa™ 6250 in accord with the FTIR spectroscopic results above.

Figure 15:
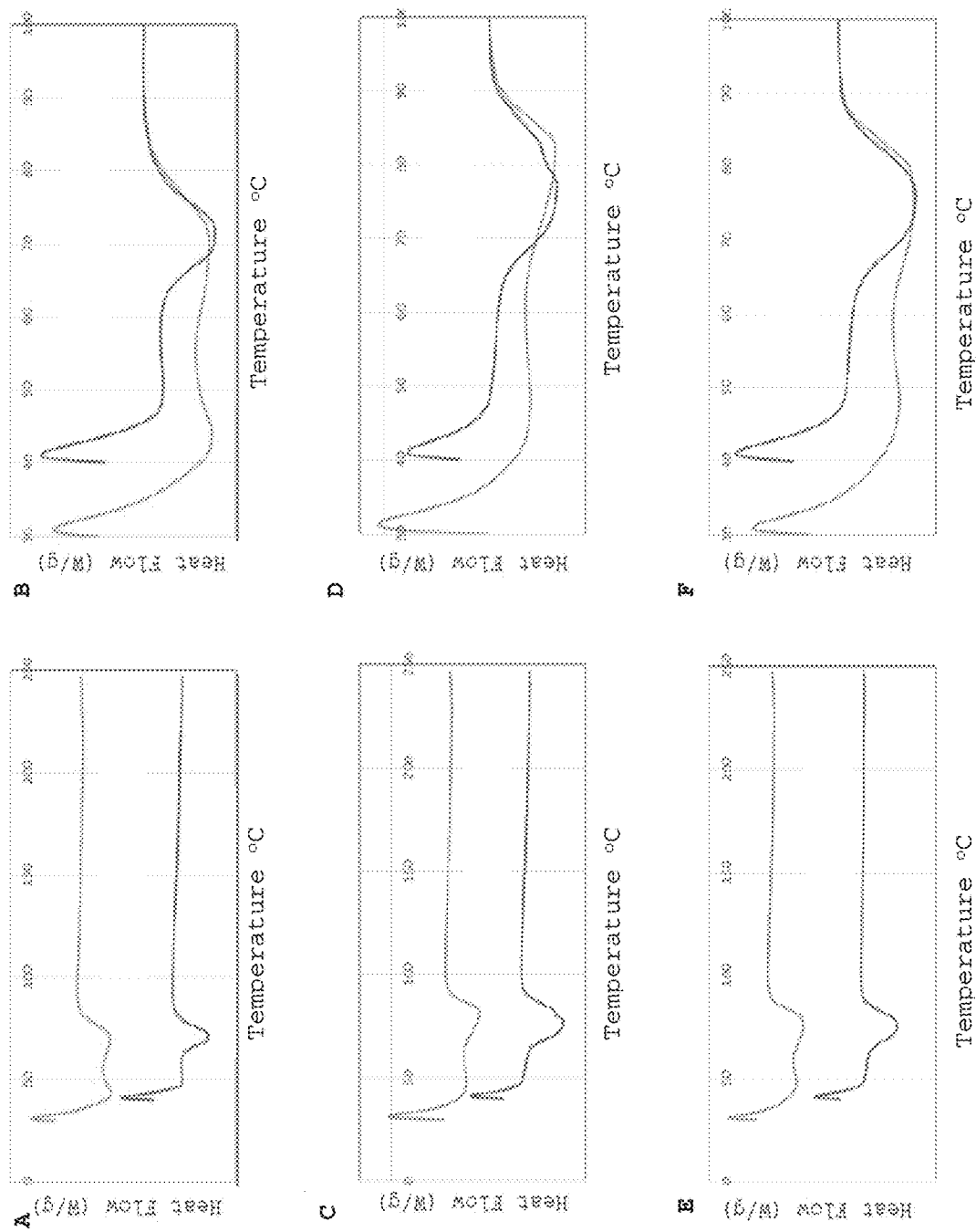
FIGS. 15A-15F show DSC plots for Elvax® 250, Elvax® 420, and Elvax® 410 barbell molded components, where

DSC plots concerning Elvax® 250, Elvax® 420, and Elvax® 410 barbell components are respectively shown in FIGS. 15A, 15C, and 15E prior to and after environmental conditioning and accelerated aging. FIGS. 15B, 15D, and 15F show an enlarged section of the resulting data that highlights the melt transition for the respective results relating to Elvax® 250, Elvax® 420, and Elvax® 410 barbell components prior to and after environmental conditioning and accelerated aging. The melting transition in the three Elvax® polymeric materials, subsequent to the ECAA testing, is narrower and concentrated to the higher temperature minima indicating an increase in the crystallite size as the distribution plot narrows.

Figure 16:
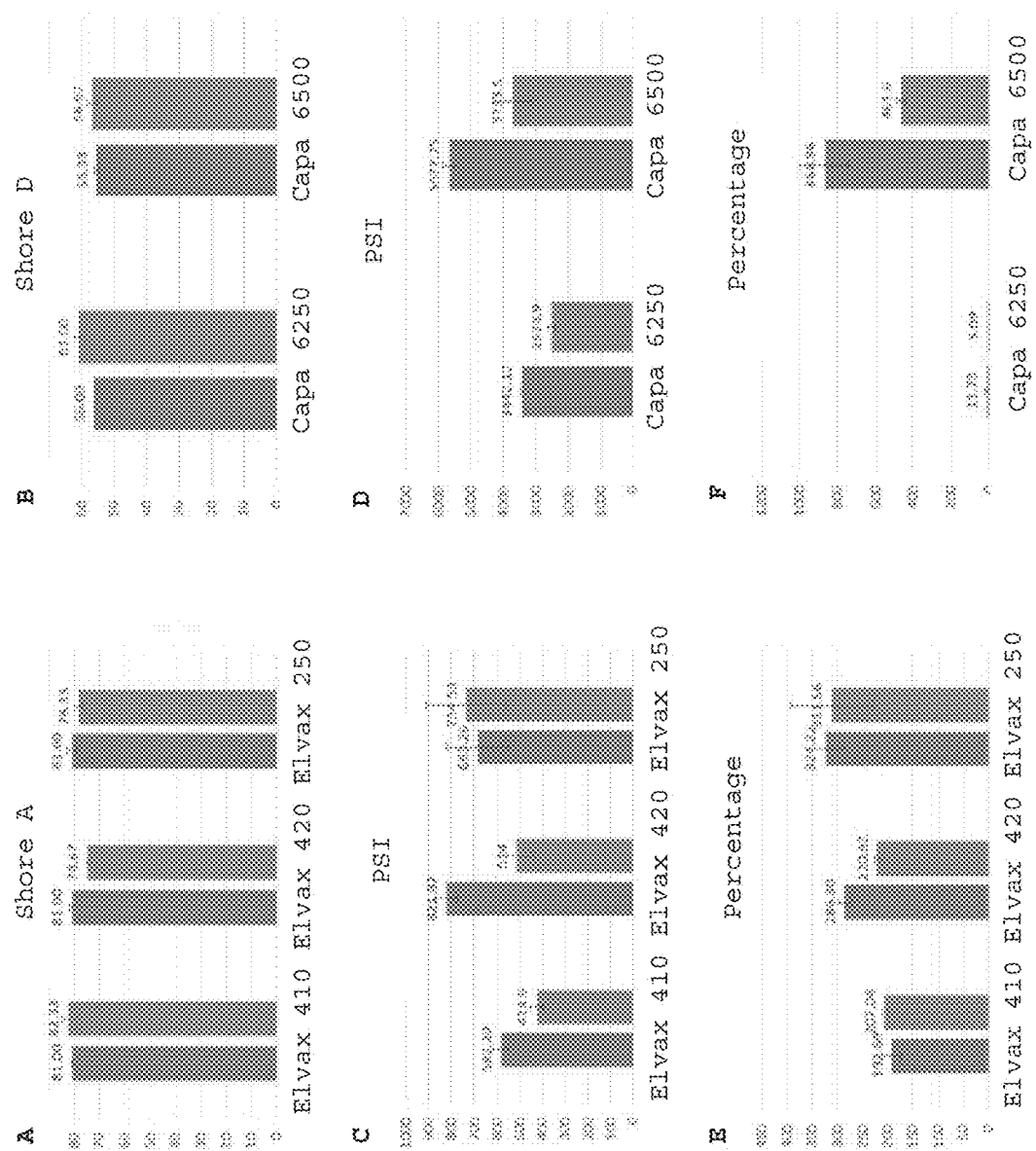
FIG. 16A details the hardness evaluation data for Elvax® 410, Elvax® 420, Elvax® 250, Capa™ 6500 and Capa™ 6250 barbell molded components.
FIG. 16B illustrates the hardness values for all five of the polymeric materials tested pursuant to Shore D parameters.
FIG. 16C shows the tensile strength concerning the Elvax® 410, Elvax® 420, and Elvax® 250 barbell components, while FIG. 16D concerns the tensile strength of Capa™ 6500 and Capa™ 6250 barbell components.
FIG. 16E shows data pertaining to the strain-at-break for Elvax® 410, Elvax®

Example 9—Environmental Conditioning and Accelerated Aging Mechanical Property Analyses Mechanical property comparisons between the barbell component prior to and after environmental conditioning and accelerated aging are shown as follows. FIG. 16A details the hardness evaluation data for Elvax® 410, Elvax® 420, Elvax® 250, Capa™ 6500 and Capa™ 6250 barbell components. FIG. 16B illustrates the hardness values for all five of the polymeric materials tested as Shore D. FIG. 16C shows the tensile strength concerning Elvax® 410, Elvax® 420, and Elvax® 250 barbell components, while FIG. 16D concerns the tensile strength of Capa™ 6500 and Capa™ 6250 barbell components. FIG. 16E shows data pertaining to the strain-at-break for Elvax® 410, Elvax® 420, and Elvax® 250 barbells, while FIG. 16F relates to the strain-at-break of Capa™ 6500 and Capa™ 6250 barbell components. In the FIG. 16 bar graphs, the left bar of the coupled comparison concerns the results prior to the ECAA testing, while the right coupled bar shows the data subsequent to ECAA testing.

Based on the mechanical properties, as detailed in FIGS. 16A-16F, it can be concluded that for all types and grades of the polymeric materials, the change in hardness value, where the maximum observed difference was approximately 7%, upon environmental conditioning and accelerated aging was determined to be markedly less compared to tensile strength, i.e., where the maximum change was observed at approximately 40%, and strain-at-break, having a maximum change at about 48%. These differences in tensile strength and strain-at-break were driven by the crystallite size increase, whereas, in contrast, the crystallite size change had minimal effect on hardness. Hence, hardness was influenced by degree of crystallinity, which by DSC and FTIR was observed, but only to a minor extent.

The tensile strength variation for the Capa™ 6500 components was observed at approximately 35%, while Capa™ 6250 possessed an approximate difference of 27%. The approximate changes for Elvax® 410 and Elvax® 420 was determined to be 40% and 27%, respectively. The tensile strength transformation relating to the high molecular weight barbells were greater than their lower molecular weight counterparts, which connotes that the crystallite size change is influenced by the molecular weight of the polymeric material. The change in tensile strength after ECAA test in Elvax® 250, moreover, was minimal indicating that the impact of vinyl acetate content was negligible.

Example 10—Integral Indicators as Single-Procedure Medical Device Components

The foregoing data and examples demonstrate the utility of the present single-use integral indicators as components of medical instruments. The guiding principle for the present indicators concerns the implementation of such indicators integral to, and as a critical component of, a medical device, which, i.e., contains polymeric materials that melt during an exposure. The most commonly employed exposure process, in this regard, is one or more steam sterilization cycles. Such melting accordingly renders the device inoperable and thus constitutes a destructive, end-of-life, indicator. As noted above, the melting behavior, thermal transition characteristics, chemical composition, and mechanical properties of the integral indicators, e.g., polycaprolactone and poly(ethylene-co-vinyl acetate), achieved the necessary requirements for the intended purpose as disclosed herein, where a directly proportional relationship between the tensile properties and molecular weight of the polymeric materials was also established. As such, the foregoing data provides valuable material properties data, and a clear understanding of what the performance characteristics must be, for the design and development of a medical device possessing an integral indicator.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 polymers refers to groups having 1, 2, or 3 polymers. Similarly, a group having 1-5 polymers refers to groups having 1, 2, 3, 4, or 5 polymers, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference herein in their entireties and for all purposes to the same extent as if each individual publication, patent, or patent application was specifically and individually incorporated by reference in its entirety for all purposes.

What is claimed is:

1. A method of manufacturing an integral indicator for a single-procedure device, comprising the steps of:
   (a) selecting a resin and/or polymeric material possessing a melting temperature ranging from about 38-109° C., a melt flow rate ranging from about 2-600 g/10 minute, a tensile strength ranging from about 20-400 MPa, a tensile modulus ranging from about 4-1000 GPa, and a strain-at-break ranging from about 4-1000%; and
   (b) forming said integral indicator with said resin and/or polymeric material, wherein said integral indicator is capable of being molded to a component of said single-procedure device and has a melting temperature ranging from about 50-121° C., a melt flow rate ranging from about 5-1000 g/10 minute, a tensile strength ranging from about 10-200 MPa, a tensile modulus ranging from about 2-500 GPa, and a strain-at-break ranging from about 4-1000%; wherein the integral indicator is configured to irreversibly transition from an operative conformation to an inoperative conformation in response to an exposure after the single-procedure.

2. The method of claim 1, wherein the integral indicator has said melting temperature, melt flow rate, tensile strength, tensile modulus, and strain-at-break following exposure to environmental conditioning and accelerated aging testing equivalent to one year at ambient conditions.

3. The method of claim 1, wherein the exposure comprises subjecting the integral indicator to: (i) one or more steam sterilization cycles, or (ii) an average temperature sufficient to precipitate the irreversible transition, or both.

4. The method of claim 1, wherein one or both of the resin and/or the polymeric material is/are selected from the group consisting of polyolefins, polyethylene, polyolefin copolymers, poly(ethylene-co-acetate), poly(ethylene-co-acrylate), polyesters, polycaprolactone and aliphatic homopolymers thereof, polyethers, polyethyleneoxide, fluoropolymers, polypropyleneoxide, olyisoprene, polyamide, polystyrene, polysulphone, polyoxymethylene, polycarbonate, polyvinyl chloride, and acrylnonitrile butadiene styrene, and filled embodiments thereof, and combinations thereof.

5. The method of claim 1, wherein the component comprises one or more non-indicator domains that: (i) are not composed of the resin or the polymeric material, or (ii) remain in the operative conformation in response to the exposure, or the combination of both (i) and (ii).

6. The method of claim 5, wherein the one or more non-indicator domains are composed of one or more materials selected from the group consisting of metals, metal alloys, shape memory alloys, titanium, nickel, copper, plastics, polymers, ceramic materials, composite materials, and stainless steel, and combinations thereof.

7. The method of claim 1, wherein the component and the integral indicator are configured as the single-procedure device, and wherein the single-procedure device is selected from the group consisting of reamers, awls, rod benders, drill guides, guide tubes, distance gages, inserters, implant holders, clamps, portals, screwdrivers, spacers, distracters, plate benders, broaches, fusion plates, fusion screws, spinal rods, spinal connectors, artificial discs, tissue-anchoring devices, fixation devices, dilators, joint spreaders, rasps, fusion cages, shavers, blades, burs, Kerrisons and Rongeurs, and combinations thereof.

* * * * *